(12) United States Patent
Hamamoto et al.

(10) Patent No.: US 6,648,822 B2
(45) Date of Patent: Nov. 18, 2003

(54) COMMUNICATION APPARATUS AND COMMUNICATION METHOD FOR OUTPUTTING AN ESTIMATE OF A PATIENT'S MENTAL STATE

(75) Inventors: Masaki Hamamoto, Sakurai (JP); Yoshiji Ohta, Kashiwara (JP); Keita Hara, Kashihara (JP); Kenji Ohta, Kitakatsurgai-gun (JP)

(73) Assignee: Sharp Kabushiki Kaisha, Osaka (JP)

( * ) Notice: Subject to any disclaimer, the term of this patent is extended or adjusted under 35 U.S.C. 154(b) by 192 days.

(21) Appl. No.: 09/904,499

(22) Filed: Jul. 16, 2001

(65) Prior Publication Data

US 2002/0105427 A1 Aug. 8, 2002

(30) Foreign Application Priority Data

Jul. 24, 2000 (JP) ........................................ 2000-222859

(51) Int. Cl.$^7$ ................................................. A61B 5/00
(52) U.S. Cl. ........................................ 600/300; 128/903
(58) Field of Search .................. 607/45, 300; 600/425, 600/508, 509, 513, 514, 528, 586; 128/903

(56) References Cited

U.S. PATENT DOCUMENTS

| 4,981,139 A | * | 1/1991 | Pfohl .......................... 600/484 |
| 5,941,829 A | * | 8/1999 | Saltzstein et al. ............ 600/509 |
| 6,287,252 B1 | * | 9/2001 | Lugo ........................... 600/300 |

FOREIGN PATENT DOCUMENTS

| JP | 1-162069 A | 6/1989 | .......... H04M/11/00 |
| JP | 5-228117 A | 9/1993 | ............. A61B/5/00 |
| JP | 10-328412 A | 12/1998 | ............. A63F/9/22 |
| JP | 11-169558 A | 6/1999 | ............. A63F/9/22 |

\* cited by examiner

*Primary Examiner*—Carl Layno
(74) *Attorney, Agent, or Firm*—Nixon & Vanderhye PC

(57) ABSTRACT

A communication apparatus includes a transmitter and a receiver for communicating communication data containing transmission data transmitted from an operator; and a data (physical data of his/her surrounding environment) analyzer for outputting a mental state and/or a physiological condition of the operator by estimating it based on the communication data. The communication apparatus enables smooth communication between a sending end and a receiving end.

25 Claims, 18 Drawing Sheets

COMMUNICATION APPARATUS AND COMMUNICATION METHOD FOR OUTPUTTING AN ESTIMATE OF A PATIENT'S MENTAL STATE

FIELD OF THE INVENTION

The present invention relates to a communication apparatus and a method which enable smooth data communication between a sending end and a receiving end.

BACKGROUND OF THE INVENTION

In conventional communication apparatuses such as a cellular phone and a facsimile, the data which are transmitted and received include mainly four types of data; namely, sound data, character data, image data, and software data. This is no different in any communication infrastructures, for example, such as the Internet, and the focus of attention has been exact reproduction of transmitted data.

However, in the prior art, the data which are transmitted and received are limited to intentional data such as the sound data, character data, image data, and software data, and a receiving end merely reproduces the received data to its original form. Thus, the receiving end cannot draw value beyond the sending end's intention from the received data.

In this connection, Japan Unexamined Patent Publication No. 228117/1993 (Tokukaihei 5-228117) (published date: Sep. 7, 1993) discloses a communication apparatus for medical use by which vital sign such as an electrocardiographic signal can be transmitted with a sound signal. Also, Japan Unexamined Patent Publication No. 162069/1989 (Tokukaihei 1-162069) (published date: Jun. 26, 1989) discloses a data communication telephone apparatus by which body sensory data such as a body temperature are transmitted with a sound signal, and the body sensory data are restored at a receiving end.

However, since the vital sign data or body sensory data are merely reproduced or restored in the conventional techniques disclosed in the foregoing publications, it is difficult and troublesome to grasp sending end's emotions or sending end's surrounding environment according to the vital sign data or the body sensory data. This poses a problem in communication between the sending end and the receiving end.

Also, no consideration is given to grasping a change in emotion or a state of surrounding environment of the sending end by the sender in the conventional techniques disclosed in the foregoing publications. This also poses a problem in communication between the sending end and the receiving end also on the side of the sending end.

SUMMARY OF THE INVENTION

It is an object of the present invention to provide a communication apparatus and a communication method which take into consideration (a) such data as vital sign data and physical data of environment which are obtained from data including sound data intentionally sent by a sending end, and/or obtained from data measured by a sensor provided on a communication apparatus provided on the sending end, and also pre-registered data in the receiving end concerning the sending end and the receiving end; and, based on these data, (b) actively calculate and estimate a mental state, a physiological condition, or a physical state of surrounding environment, such as feelings or emotions (happy, angry, sad, pleasant), a physical condition, and surroundings of the sending end, and (c), for example, display numeric values, figures, and drawings, or a superimposed image of these images on an image of the sending end with respect to the receiving end (or sending end), so as to enable more steady communication.

In order to achieve the foregoing object, the communication apparatus according to the present invention includes a transmitter and a receiver for communicating communication data including transmission data concerning an operator; and an estimating section which estimates a mental state and/or a physiological condition of the operator and outputs the estimation as an estimated quantity.

According to the arrangement, the transmission data concerning the operator, for example, such as sound data, image data, character data, and software data can be communicated by the transmitter and the receiver.

Further, according to the arrangement, in the estimating section, the estimated quantity regarding feelings or emotions, a state of health, and surrounding environment of the operator on the side of the sending end can be extracted and outputted.

Thus, in the arrangement, the receiving end not only receives transmission data concerning the operator, but also complements, based on the estimated quantity unintentionally sent from the sending end, the transmission data with the outputted estimated quantity to realize further understanding. As a result, the arrangement enables communication to be deeper and more effective.

In order to achieve the foregoing object, the communication method of the present invention estimates a mental state and/or a physiological condition of the operator based on the communication data and outputs the estimation, when an operator communicates communication data including transmission data concerning the operator.

Since the method makes it easier for the receiving end (and/or the sending end) to grasp the sending end's feelings and emotions, a state of health, and his/her surrounding environment, communication between the sending end and the receiving end can be made smooth.

For a fuller understanding of the nature and advantages of the invention, reference should be made to the ensuing detailed description taken in conjunction with the accompanying drawings.

DESCRIPTION OF THE EMBODIMENT

Embodiments of the present invention are described below based on FIG. 1 to FIG. 18.

Figure 1:
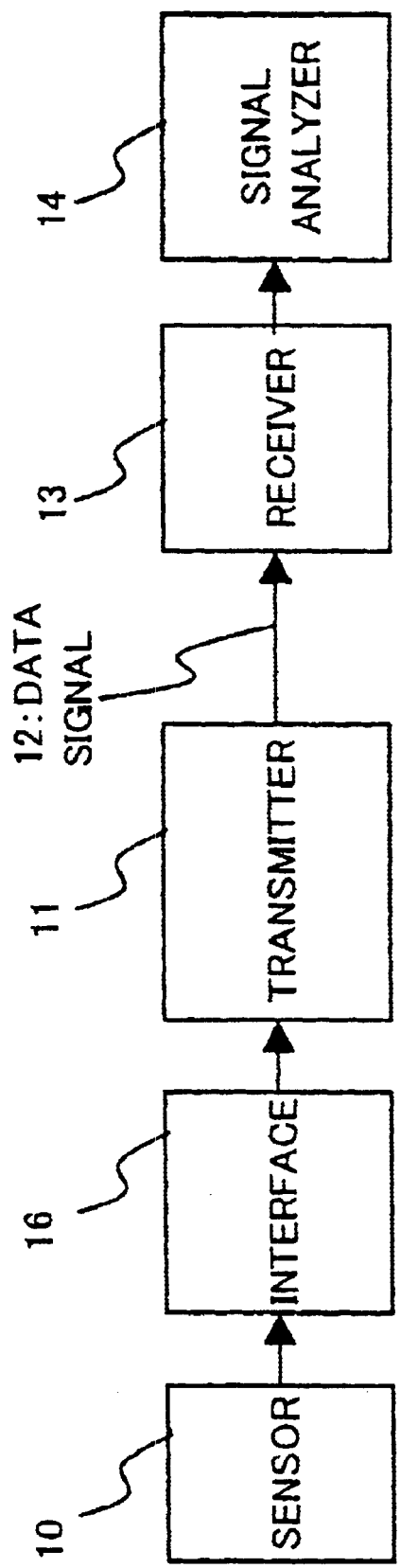
FIG. 1 is a schematic block diagram of a communication apparatus of the present invention.

As shown in FIG. 1, a communication apparatus has a transmitter 11 in which communication data 12 including transmission data such as sound data and image data are inputted and are transmitted; a receiver 13 which receives and outputs the transmitted communication data 12; and a data (physical data of surroundings) analyzer 14 as an estimating section which extracts and estimates data indicative of a state of an operator, or physical data of surrounding environment from the transmitted data and outputs the estimation as an estimated quantity.

The communication data 12 transmitted from the transmitter 11 of a sending end is received by the receiver 13 of the receiving end, and the transmission data, for example, such as sound data or image data included in the communication data 12 are outputted to an operator of the receiving end and processed in the data (physical data of surroundings) analyzer 14 to extract and estimate a mental state and/or a physiological condition of the operator based on the communication data 12, and the extracted and estimates data are outputted to the operator of the receiving end.

The communication apparatus of the present invention not only decodes (convert transmitted data back to an original form of before-transmitting) as in a decoder of conventional communication apparatuses, but also estimates a mental state and/or physiological condition of the operator and a physical state of surrounding environment of the operator based on the communication data 12. Thus, a sensor 10 which measures vital sign data and/or physical data to estimate a mental state and/or a physiological condition of the operator at the receiving end, or a physical state of surrounding environment of the operator at the receiving end is provided as required. The sensor 10 is described below concretely.

Figure 2:
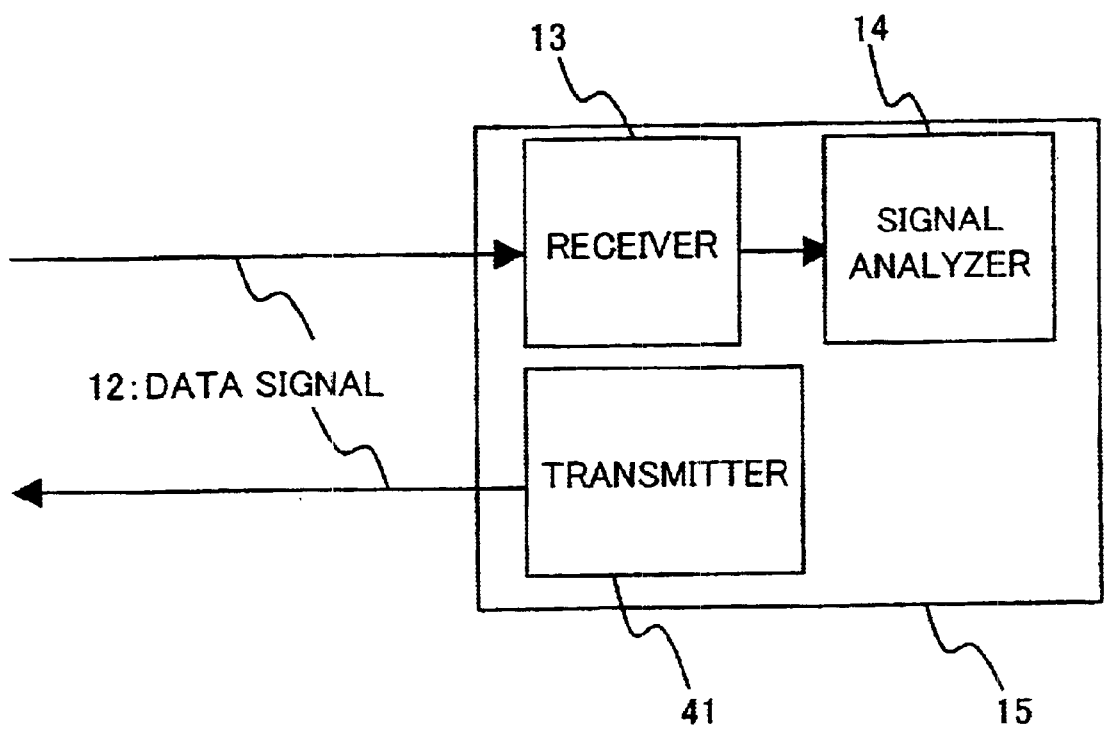
FIG. 2 is a schematic block diagram showing how bidirectional communication is realized with the communication apparatuses.

FIG. 2 is another embodiment in which the communication apparatus of FIG. 1 is made bidirectional. When functions of the present invention are applied to a current cellular phone, for example, as shown in FIG. 2, a communication apparatus body 15 such as a casing 15 includes the receiver 13, the data (physical data of surroundings) analyzer 14, and a transmitter 41 having almost the same function as the transmitter 11.

Figure 3:
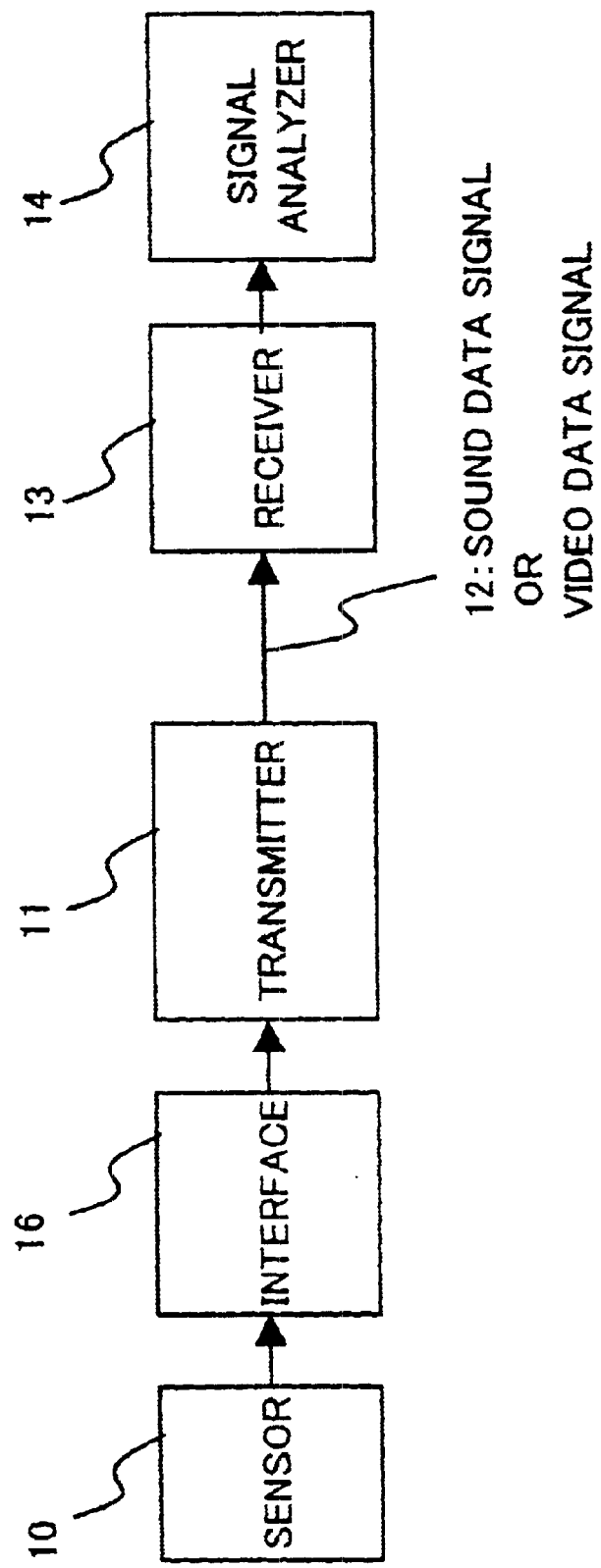
FIG. 3 is a schematic block diagram when communication data of the communication apparatus includes sound data or image data.

Next, FIG. 3 is still another embodiment in the case where the communication data 12 are sound data or image data. In current cellular phones, for example, transmission data are limited mainly to sound data, or in the case of near-future cellular phones, data which can be added to the sound data will be limited to image data. Thus, in application to cellular phones, it is convenient to extract (estimate) an estimated quantity based on either or both of sound data and image data by using the data (physical data of surroundings) analyzer 14.

In this case, the operator's feelings or emotions, and a state of his/her health, and surroundings can be estimated based on (a) sound data frequency of voice (high-low), intensity (energy density), a voiceprint, intonation, speed of speech, level of excitement, and timing of response, etc. in the case of sound data and based on (b) direction of view, blinks, pupil size, movement of lips, moisture of mouth or lips, facial expressions and colors, movement of body, a posture, the number of people present around the apparatus, brightness, and weather etc. in the case of image data. Estimation according to both sound and image data is more effective.

Figure 4:
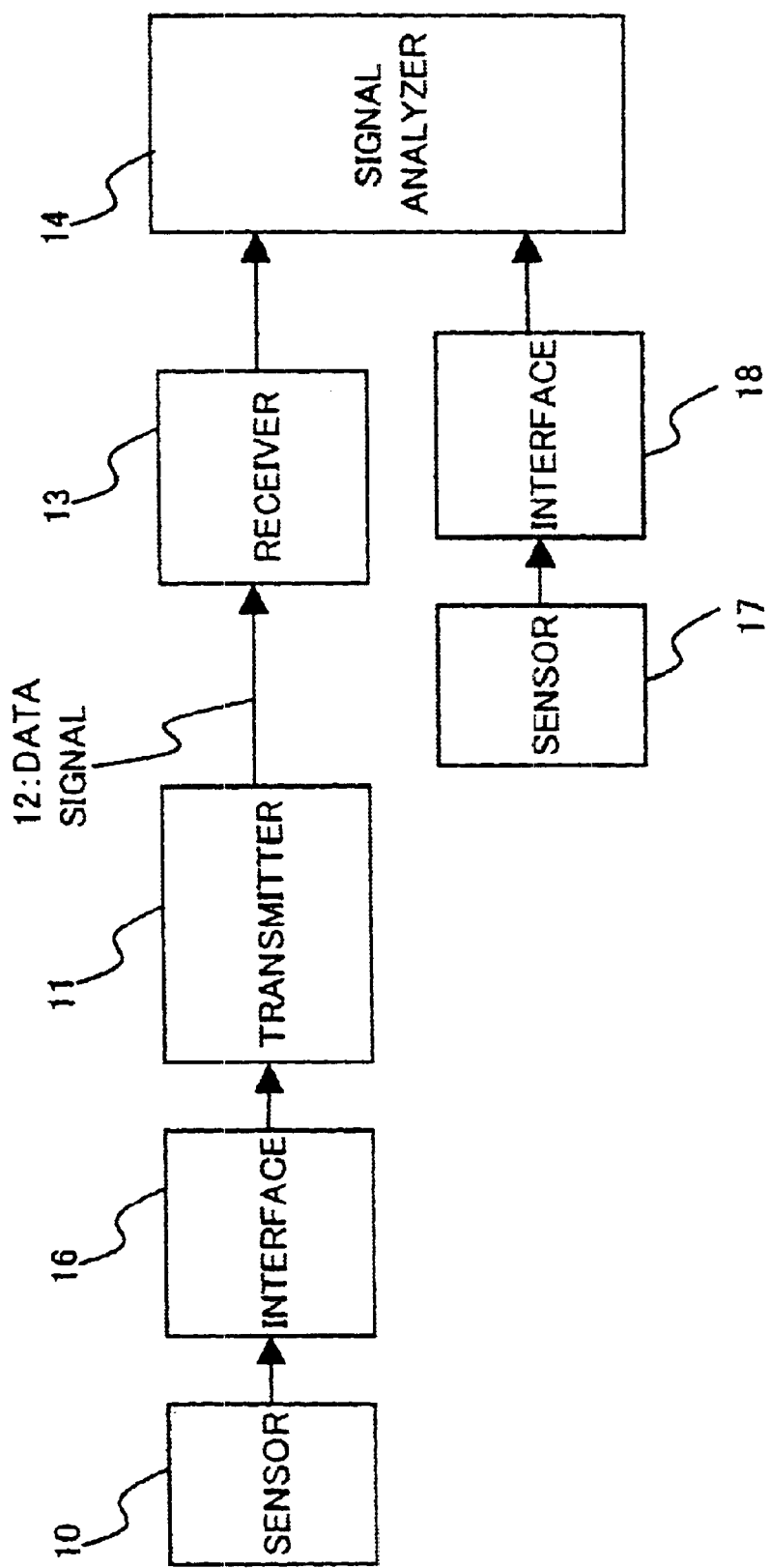
FIG. 4 is a schematic block diagram showing an example where a sensor is also provided in a receiving end in the communication apparatus.

FIG. 4 is still another embodiment in which not only sound data and image data but also various other data are measured so as to extract data more exactly. The vital sign data and the physical data which are indicated by an electrical resistance value measured by the sensor 10, or a physical quantity equivalent to the electrical resistance value (e.g., voltage value, current value, and potential difference) are transmitted with the communication data 12 from the transmitter 11 and received by the receiver 13. These transmitted data are then used to estimate, for example, emotions such as a mental state and physiological condition of the operator by the data (physical data of surroundings) analyzer 14.

Concrete examples of this include brain waves, magnetoencephalography (MEG), blood pressure, heartbeats, rate of respiration, skin resistance value, sweating, body temperature, distribution of body temperature, vibration of components such as the communication apparatus body 15, temperature, humidity, air pressure, wind force, wind direction, brightness, purity of air, longitude and latitude, altitude, and sound.

Next, when communication is bidirectional, a sensor 17 which functions in the same manner as the sensor 10, and an interface 18 are provided at the receiving end in still another embodiment shown in FIG. 4 because this allows various estimations to be performed based on a clearer response of the receiving end (a mental state, a physiological condition, and physical data) with respect to communication data transmitted by the sending end. It is clear that either or both of the sensor 10 and 17 may be used.

Also, by providing the sensor 10 and/or 17 on a support portion (a portion in contact with or close to the operator) of either or both of the sending end and receiving ends in communication apparatus bodies 15, the vital sign data concerning the operator of the sending end or receiving end can be detected more exactly and more naturally.

Figure 5:
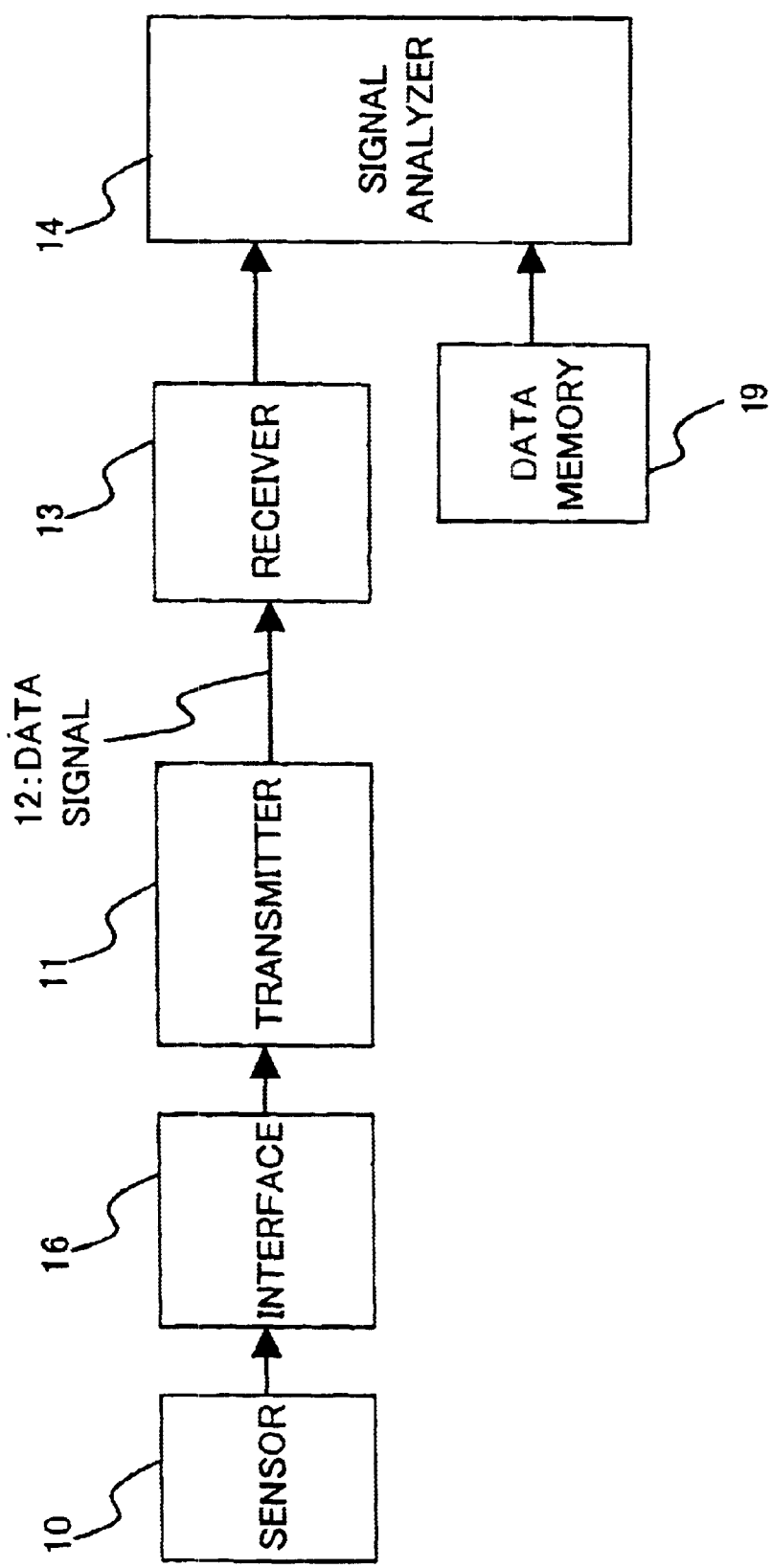
FIG. 5 is a schematic block diagram showing an example where a data memory for storing learned information is provided in the receiving end in the communication apparatus.

Next, FIG. 5 shows still another embodiment in which, in addition to the communication data 12 which are obtained in communication, known data of the sending or receiving end are stored in the receiving end in advance and used to estimate a mental state and/or a physiological condition of the operator, or a physical state of surrounding environment of the receiving end.

In this embodiment, when extraction is performed by the data (physical data of surroundings) analyzer 14, not only data in communication which are obtained by the receiver 13, but also the known data, for example, such as the telephone number, sex, and age of the sending or receiving end, and a social relationship between the sending and receiving ends which are stored in a data memory 19 are used. Though not shown, the data memory 19 may be provided on the side of the sending end, and the receiving end may obtain the known data as communication data from the sender.

Figure 6:
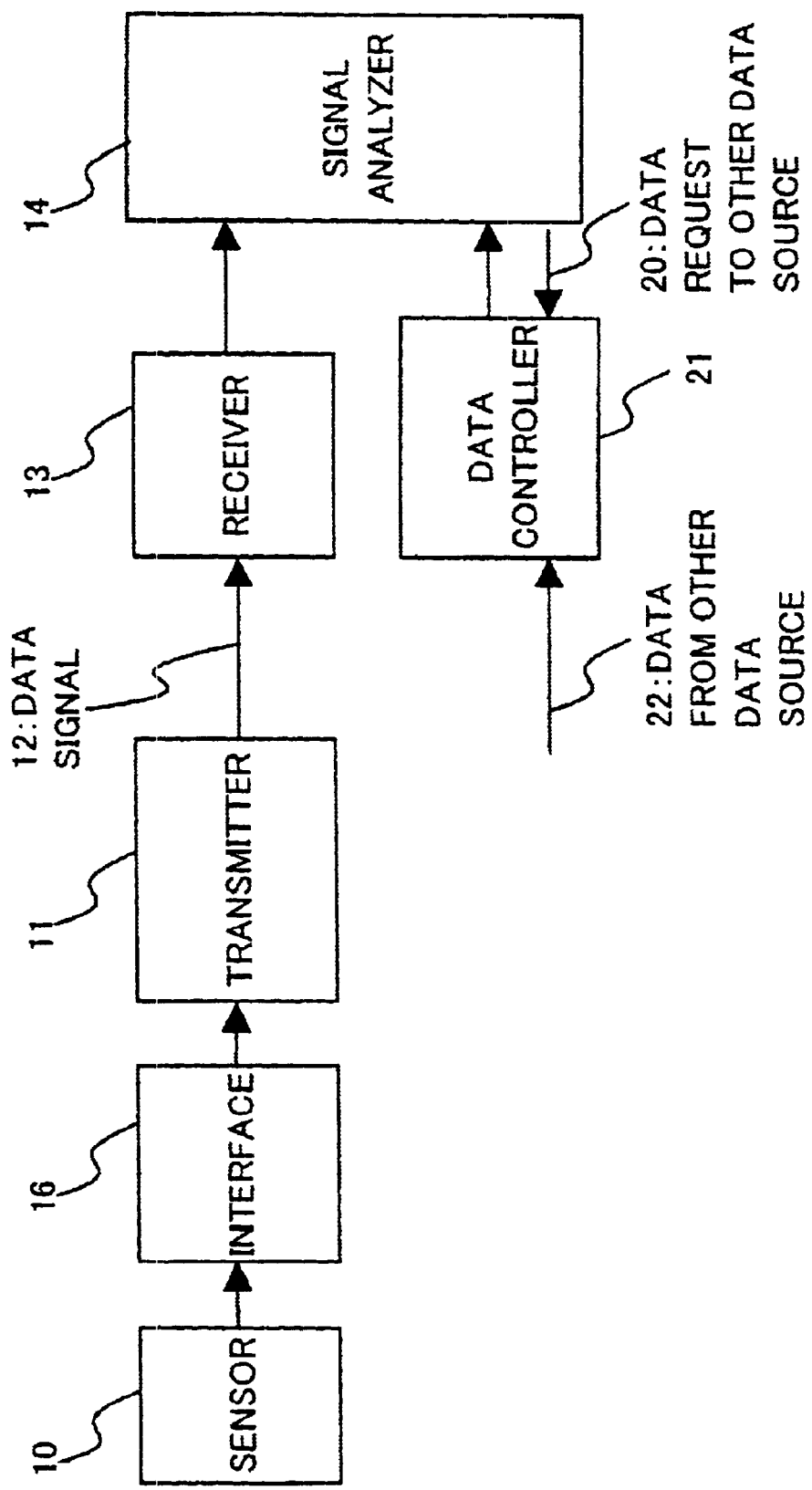
FIG. 6 is a schematic block diagram showing an example where a data controller is provided in the receiving end in the communication apparatus.

Further, FIG. 6 shows still another embodiment in which not only the data of the receiving end and the sending end, but also data of a third party are obtained. In this embodiment, when data of the third party are needed in the data (physical data of surroundings) analyzer 14, a data request to the third party (third-party data request) 20 is outputted from the data (physical data of surroundings) analyzer 14 and received by a data controller 21. In response, the data controller 21 obtains communication data 22 from the third party and outputs the data to the data (physical data of surroundings) analyzer 14. Examples of this application include access to a server as a database having a large capacity, and data collection via a network as represented by the Internet.

Figure 7:
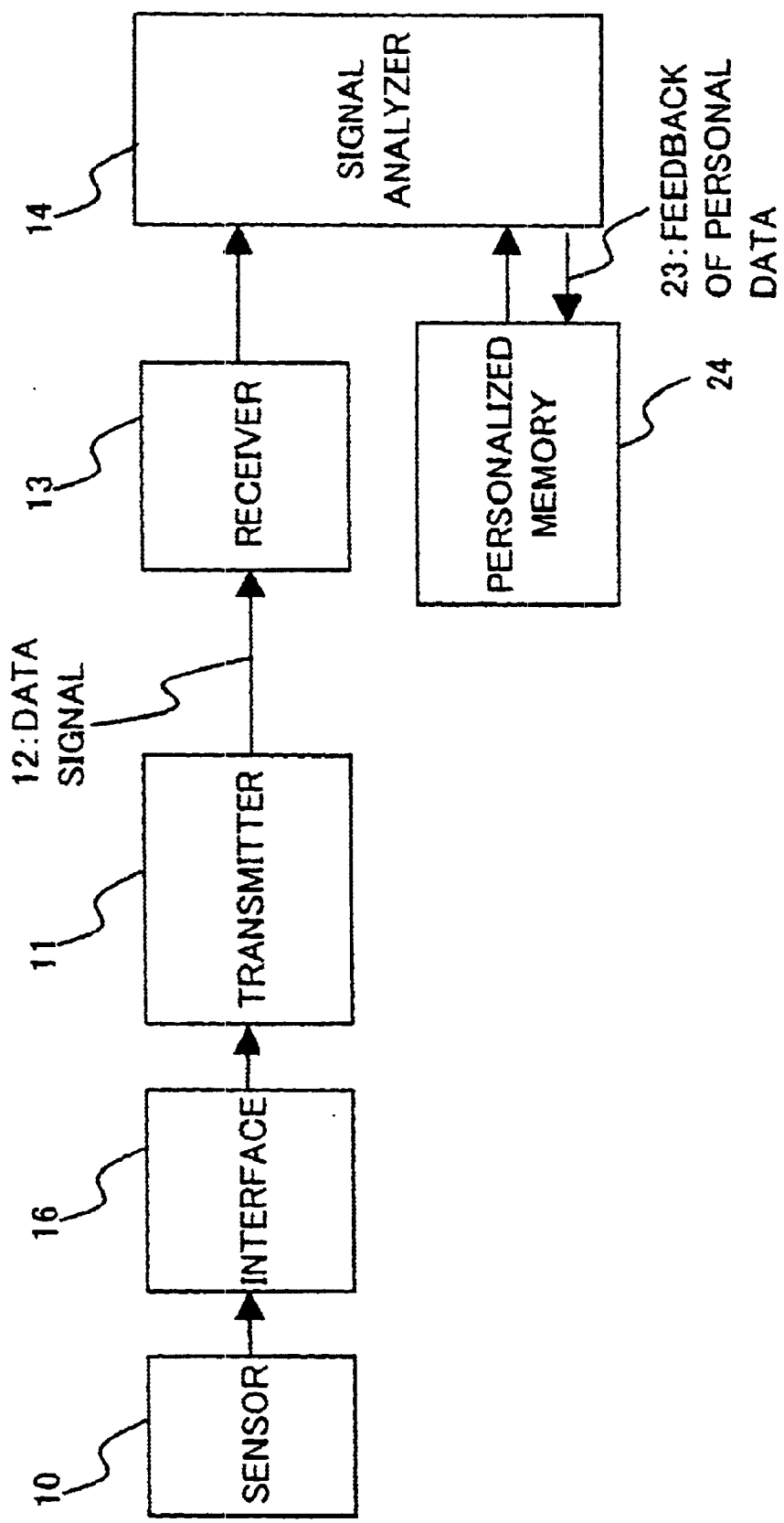
FIG. 7 is a schematic block diagram showing an example where a personalized memory is provided in the receiving end in the communication apparatus.

Next, FIG. 7 shows still another embodiment in which results of communications are stored with respect to each operator, and are used to process the data (physical data of surroundings) in subsequent communications. In this embodiment, a result given by the data (physical data of surroundings) analyzer 14 is stored as feedback on personal data (personal data feedback) 23 with regard to the processed content in the personalized memory 24. According to this, data needed for the processing are updated, and algorithm for processing data is learned.

Figure 8:
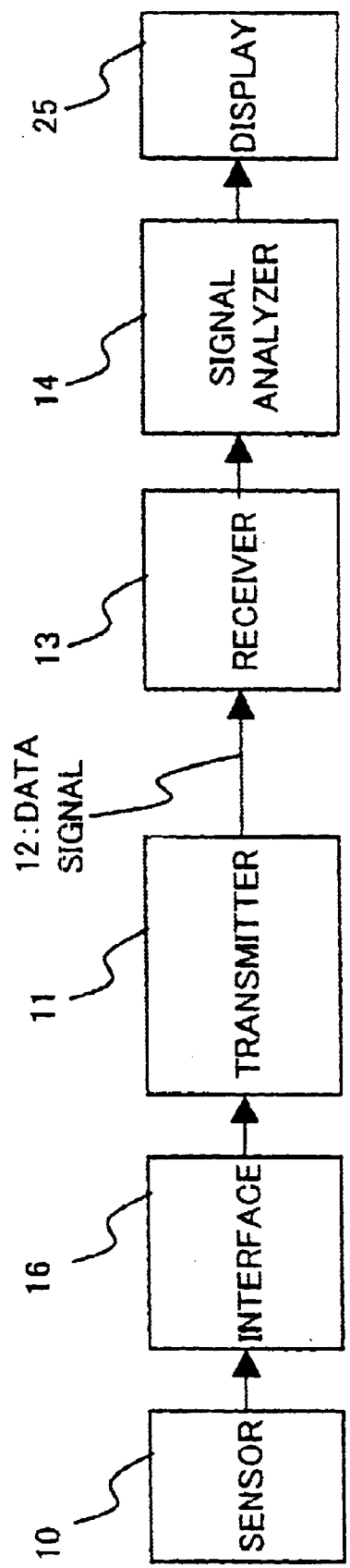
FIG. 8 is a schematic block diagram showing an example of the communication apparatus provided with a display.

Next, FIG. 8 shows still another embodiment in which a display 25 is provided to make it easier for the receiving end to understand a processed content. In this embodiment, the display 25 such as a liquid crystal display for displaying a result of processing by the data (physical data of surroundings) analyzer 14 is provided. Though FIG. 8 shows the embodiment in which the display 25 is added to FIG. 1, it is clear that the display 25 can be added to any of FIG. 2 through FIG. 7.

FIG. 9 to FIG. 14 show examples of drawings and graphs which indicate estimated quantities displayed on the display 25. For example, when emotions and the like of the sending end are displayed, some parameters (data signals and physical data) are used to display them. Taking FIG. 10 as an example, a parameter 1 on the axis of ordinate indicates "strength and weakness of emotions (stronger in positive direction)", and a parameter 2 on the axis of abscissa indicates "pleasant and unpleasant (more pleasant in positive direction)", wherein the first quadrant represents "happy", the second quadrant represents "angry", the third quadrant represents "sad", the fourth quadrant represents "pleasant". A mark 27 indicated by a calescence point indicates a state of mind such as "happy", "angry", "sad", or "pleasant", and a degree of these different states of mind, i.e., emotion. Thus enabling an operator of the receiving end to grasp emotions more easily.

Figure 9:
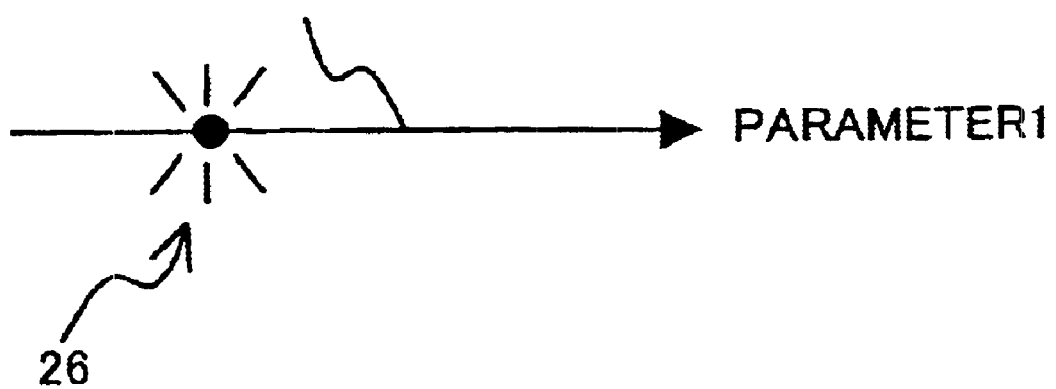
FIG. 9 is an explanatory drawing showing a display example of the display in the communication apparatus.

A mark 26 and a mark 28 indicated by calescence points can indicate emotions as long as the parameters are set appropriately even in such cases as when the number of the axis is larger (see FIG. 11) or smaller (see FIG. 9). A graph 29 may indicate emotions as shown in FIG. 12 or a radar chart 30 also may indicate emotions as shown in FIG. 13.

Figure 13:
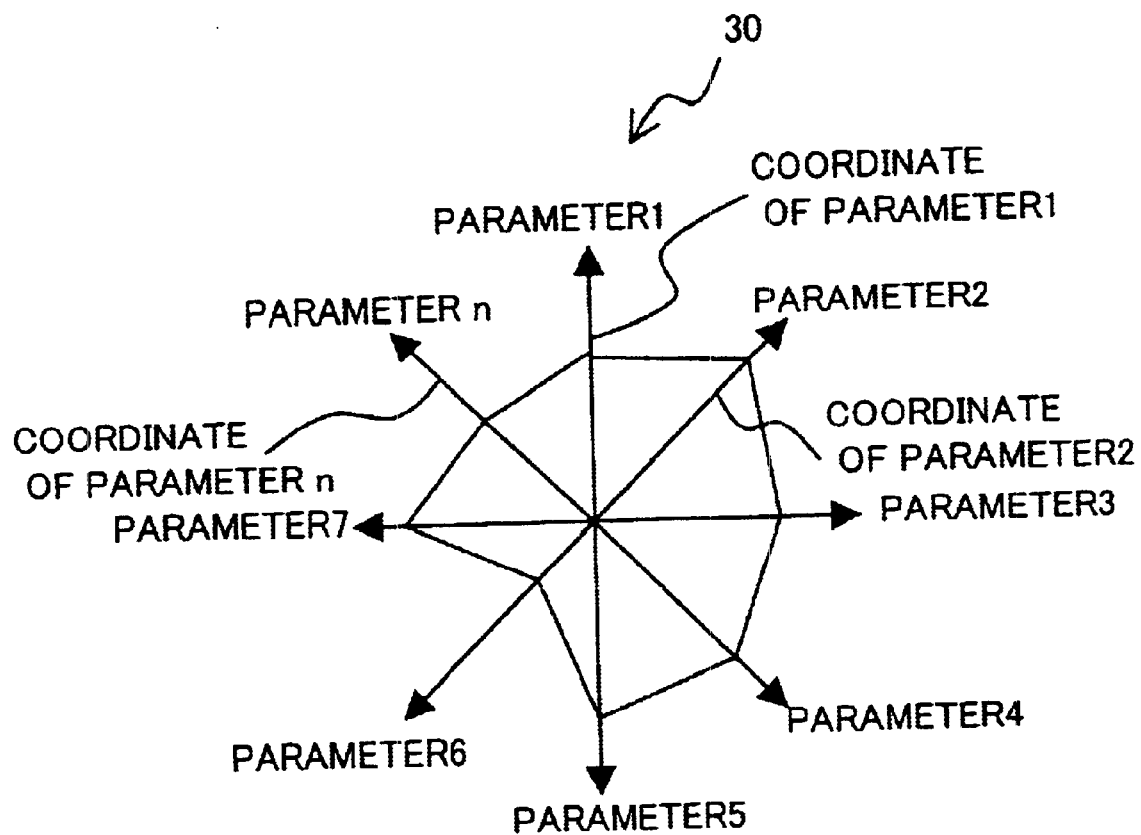
FIG. 13 is a radar chart showing still another display example of the display in the communication apparatus.
Figure 14:
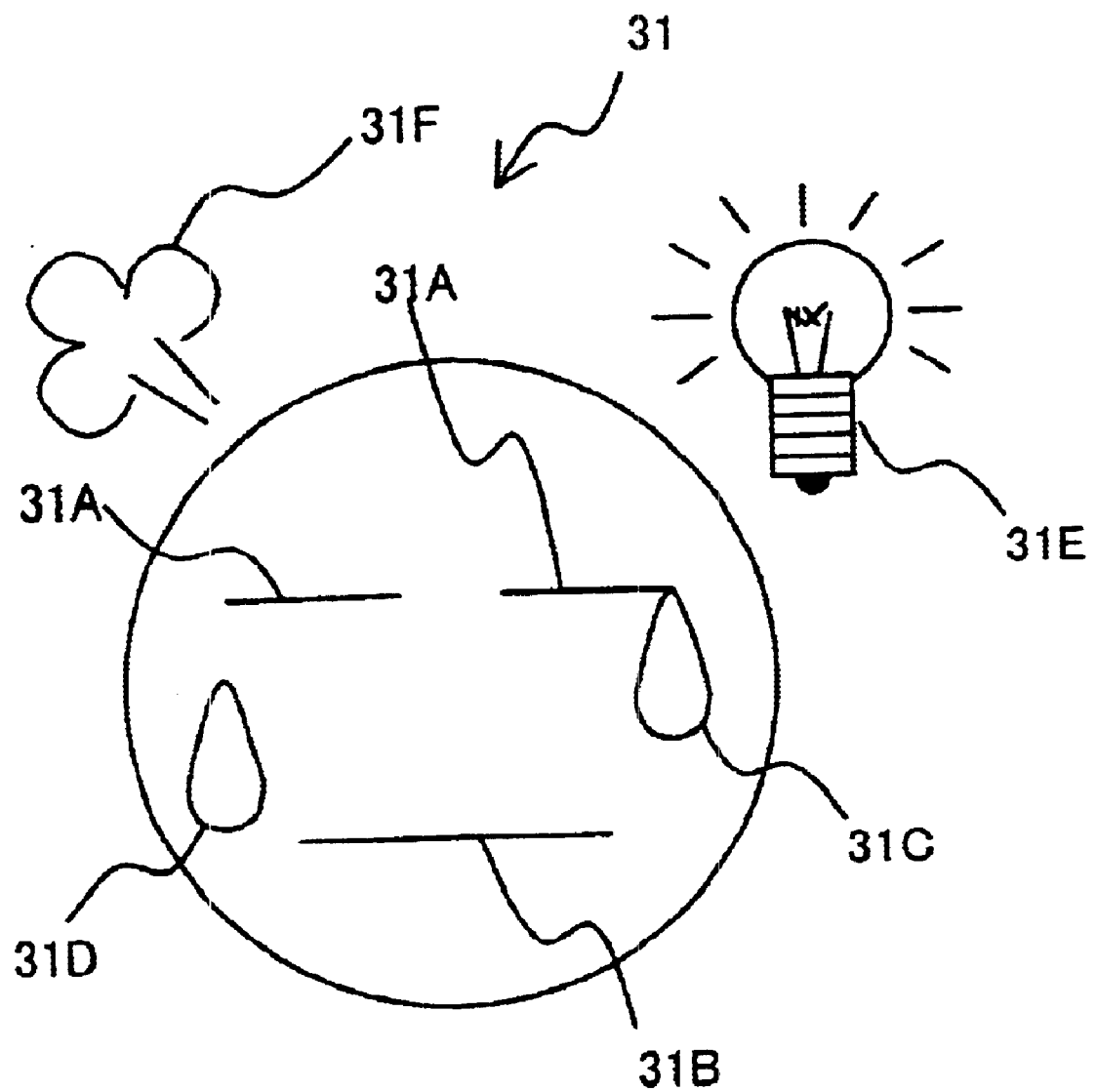
FIG. 14 is an explanatory drawing showing still another display example of the display in the communication apparatus.

As a more familiar example, a display using a drawing (illustration) of a face 31 as shown in FIG. 13 may be useful. The drawing (illustration) 31 shown in FIG. 14 displays, for example, a shape of eyes 31a, a shape of a mouth 31b, a teardrop 31c, a cold sweat 31d, a flash of a light meaning "eureka!" 31e, a cloud-shaped blowing meaning "anger" 31f, so as to indicate the emotions of the operator of the sending end. Other various expressions such as a distribution figure, a doughnut figure, and a circle graph can be used.

The important thing in a display like this is that some specified parameters represent various emotions to indicate a mental state and/or physiological condition of the sending end, or physical state of surrounding environment. Displaying these images side by side with or over the actual images of the sending end is very useful for the receiving end in grasping circumstances of the sending end.

Figure 15:
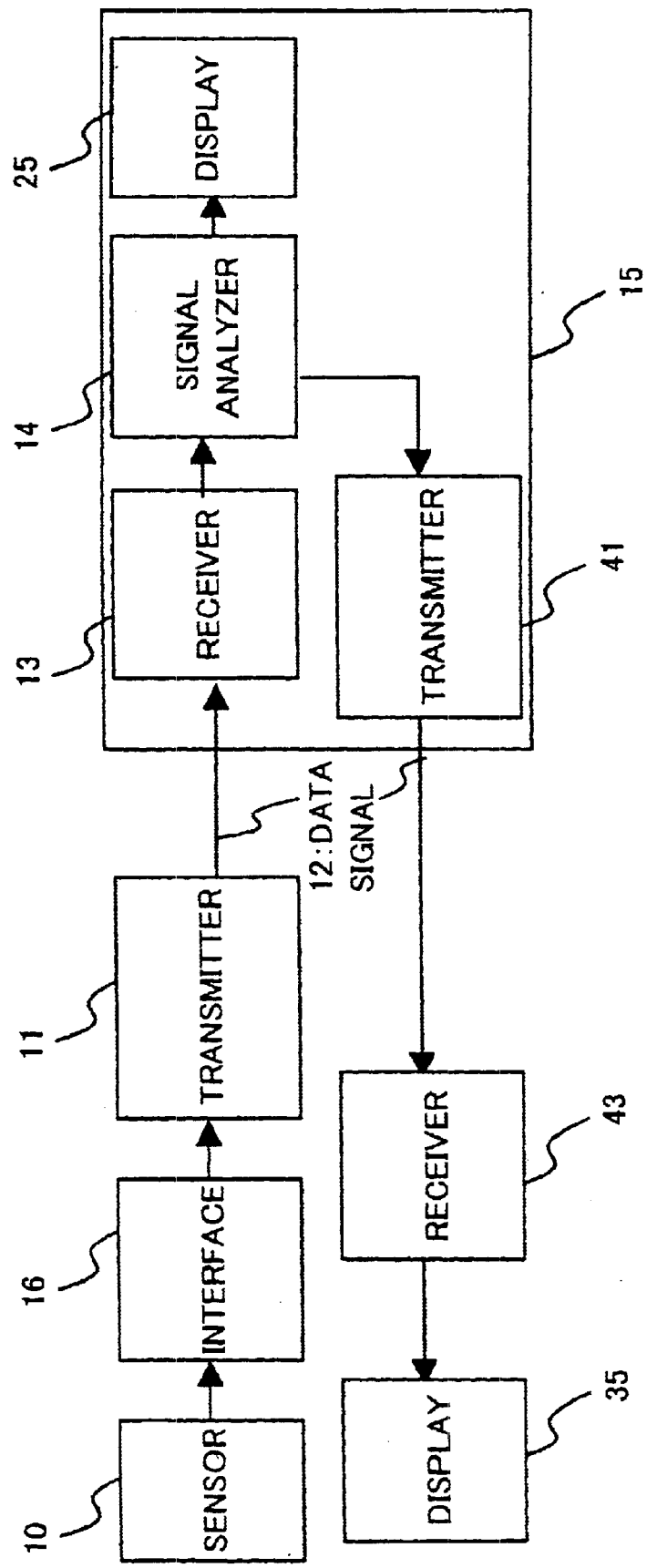
FIG. 15 is a schematic block diagram showing an example where the display is also provided in the sending end in the communication apparatus.
Figure 16:
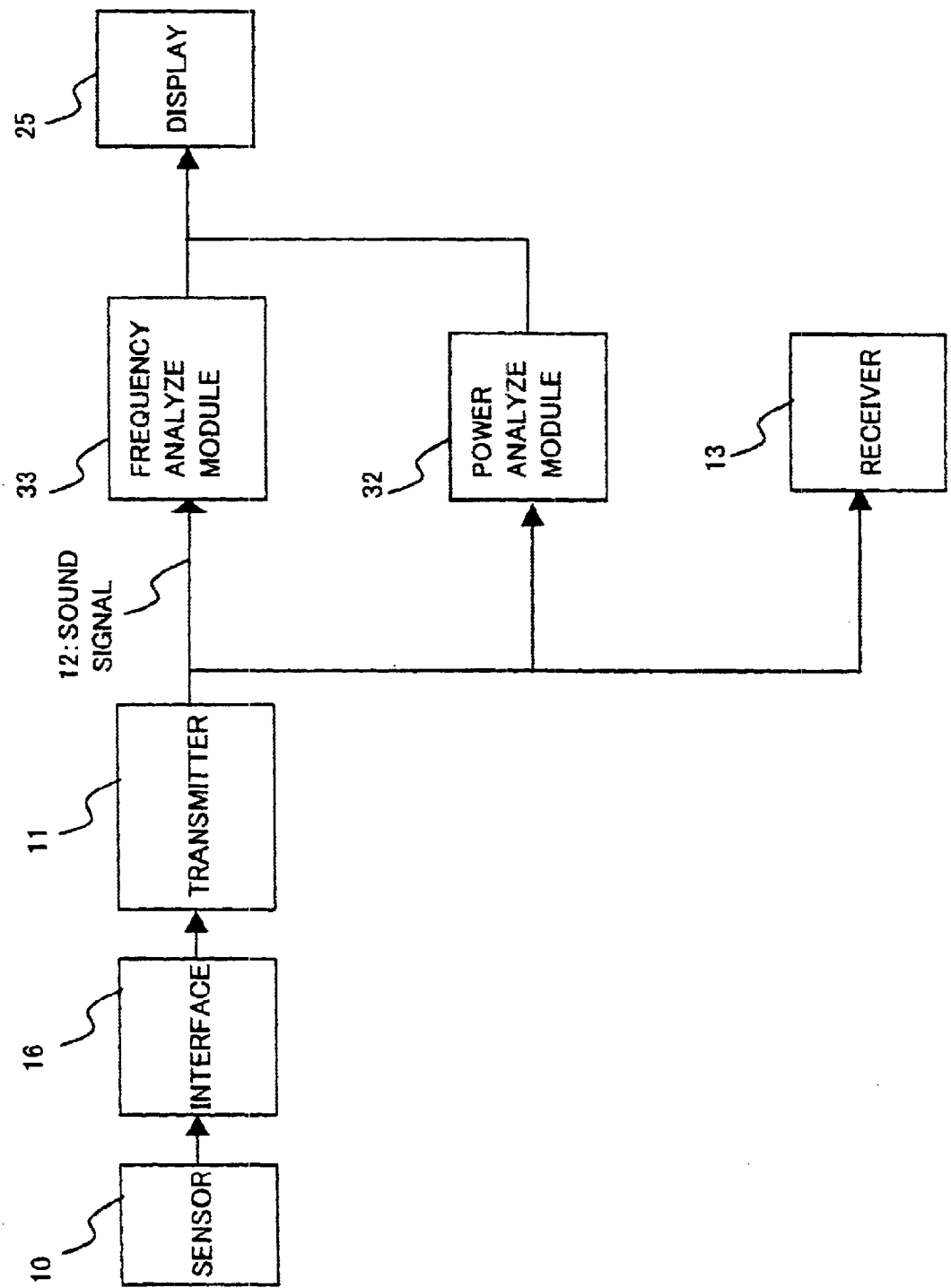
FIG. 16 is a schematic block diagram showing an example of analyzing sound data in the communication apparatus.

FIG. 15 shows still another embodiment in which the display can also be seen by the sending end. In this embodiment, the result of processing by the data (physical data of surroundings) analyzer 14 is outputted not only to the display 25 of the receiving end, but also to a display 35 of the sending end via a transmitter 41 and a receiver 43. Since the sending end can monitor how data are received by the receiving end, appropriate feedback is made possible.

The display 35 functions in the same manner as the display 25 of the receiving end. Also, the display screens of the display 25 and the display 35 are preferably provided with transparent input sections of a touch panel type so as to provide switch functions described later, and an entry function which functions as a switch for turning on and off various functions by allowing the operator to input data through icons and the like on the display screen which are touched directly with the operator's hand or via an input pen.

Since a display like this could be judged to be unnecessary or inpreferable at the sending or receiving end, it is preferable to mutually control permission of the display. Though the embodiments based on FIG. 3 to FIG. 15 are described with reference to the figures based on FIG. 1, it is clear that the bidirectional arrangement of FIG. 2 can be applied to these figures.

The sensor 10 is described below, according to the parameters which are to be measured by the sensor 10. The sensor 10 for measuring a mental state and physiological condition of the operator detects vital sign data of at least one item which is selected, for example, from the group consisting of: a brain wave which is used to detect activity of the operator's brain, frequency of blinks, electrical resistance of skin (hereinbelow referred to as skin resistance), amount of sweat, tone, movement or moisture of a mouth, movement of a head, pupil size, facial expressions, heartbeats, rate of respiration, state of respiration, and body temperature.

For example, a brain wave is measured as the vital sign data as below. The brain wave has four representative frequency bands. They are $\delta$ wave (0.5 to 4 Hz), $\theta$ wave (4 to 8 Hz), $\alpha$ wave (8 to 14 Hz), $\beta$ wave (14 to 30 Hz). The $\delta$ wave appears during sleep, the $\theta$ wave while relaxing deeply in meditation and the like, the $\alpha$ wave while feeling at home and relaxing, or while relaxing due to a concentration, for example, when memorizing something, and $\beta$ wave while feeling nervous.

One of the methods for detecting a brain wave, for example, is to simply detect a slight change of skin electric potential between a skin of the forehead and a skin of an ear (for example, a skin of an earlobe) by using a head band touching the skin of the forehead and an ear-electrode touching the ear.

When an operator of the communication apparatus wants to transmit his/her mental state and/or physiological condition to the receiving end, or when the operator communicates while checking his/her mental state and/or physiological condition, the sensor 10, which detects the brain wave in the foregoing manner, is connected to an interface 16. Thus vital sign data based on the brain wave can be measured and included in the communication data 12 to be transmitted to the communication apparatus.

Figure 10:
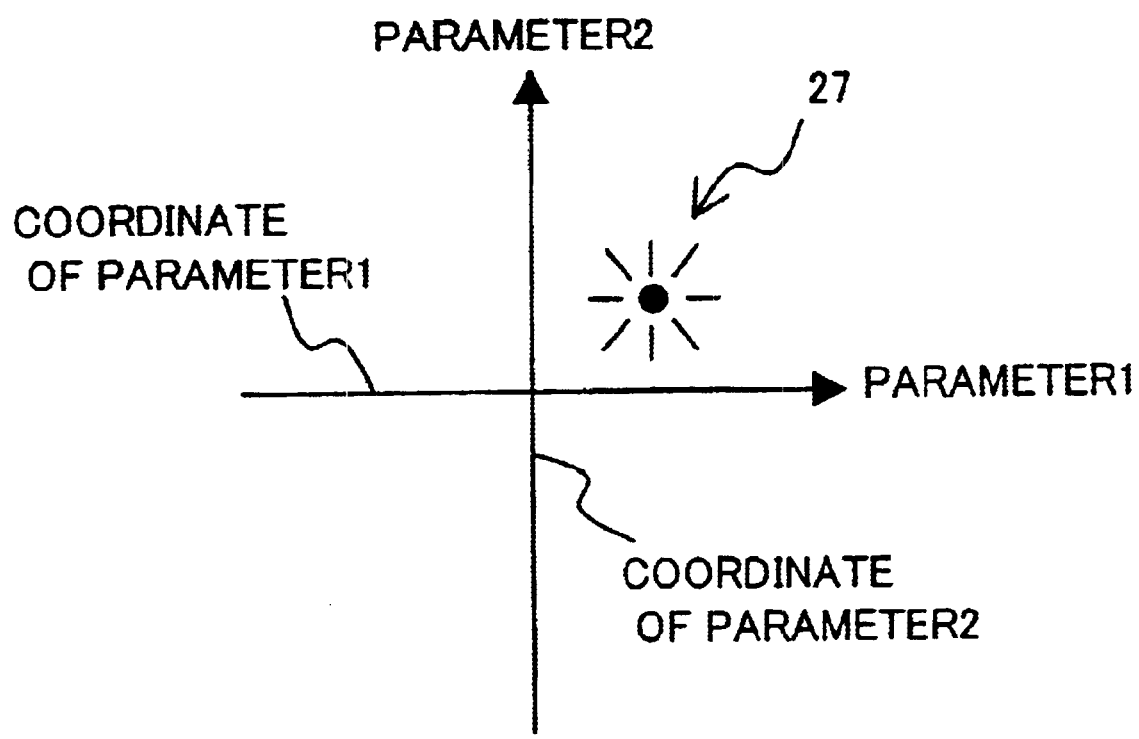
FIG. 10 is an explanatory drawing showing another display example of the display in the communication apparatus.

The vital sign data of the brain wave thus detected by the sensor 10 are analyzed with respect to frequency in the data (physical data of surroundings) analyzer 14 of the receiver 13, and basically categorized into the four representative frequency bands, and as shown in FIG. 10 and FIG. 12, the sending end's emotions are displayed based on the frequency bands.

For example, when the brain wave is the only parameter displayed, only one parameter is displayed, so that the displacement is one-dimensional either in the direction of ordinate or abscissa. However, when another parameter is added for a multivariate analysis, the parameters are displayed two-dimensionally.

Figure 18:
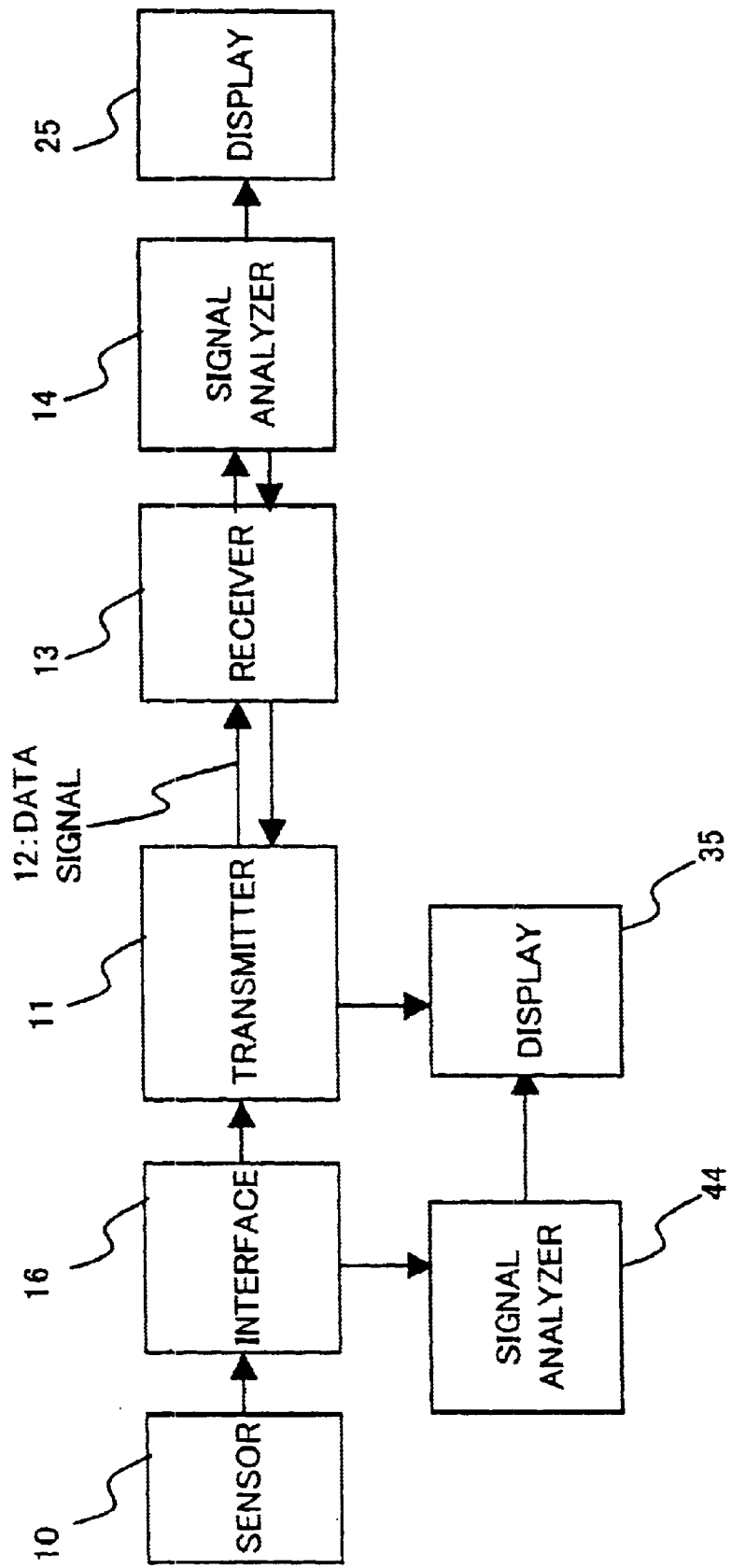
FIG. 18 is a schematic block diagram showing an example where a data (physical data of his/her surroundings) analyzer and the display are provided also in the sending end in the communication apparatus.

Next, as shown in FIG. 18, a modification example of the embodiment is described. That is, it is the case where the sending end's emotions are displayed also on the side of the sender (on the side of the sensor). A data (physical data of surroundings) analyzer 44 which functions in the same manner as the data (physical data of surroundings) analyzer 14, and a display 35 which functions in the same manner as the display 25 of the receiving end are provided also on the sender side and the data of brain wave frequency analyzed by the data (physical data of surroundings) analyzer 44 are set to be sent to the display 35 of the sender for display. Alternatively, the data of the brain wave frequency analyzed by the data (physical data of surroundings) analyzer 44 may be sent to the receiver 13, and displayed on the display 25 of the receiver 13.

In this case, a mental state and/or a physiological state of the sending end analyzed according to the brain wave can be displayed on both the sending and receiving ends. However, even in this case, the transmitter 11 of the sending end can be provided with a switch for permitting or not permitting the apparatus to transmit data of the mental state and/or a physiological condition of the operator; or the receiver 13 of the receiving end can be provided with a switch for permitting or not permitting the apparatus to receive the data; or the display 35 of the receiving end can be provided with a switch for permitting or not permitting the apparatus to display data of the mental state and/or the physiological state of the operator; or the display 25 of the receiving end can be provided with a switch for permitting or not permitting the apparatus to display the data of the mental state and/or the physiological condition of the operator. Thus, the operator can restrict display of the data of the operator's mental and/or physiological state intentionally.

Alternatively, the vital sign data of the brain wave detected by the sensor 10 are transmitted from the transmitter 11 without being analyzed and processed, and received by the receiver 13 and analyzed with respect to frequency in the data (physical data of surroundings) analyzer 14 of the receiver 13, and categorized into basically the four representative frequency bands mentioned above. Thereafter, as shown in FIG. 10 and FIG. 12, the data are displayed on the display 25 based on the frequency bands.

Another modification example is as follows. When displaying on the side of the sender, the data of the analyzed brain wave frequency measured by the sender and analyzed by the data (physical data of surroundings) analyzer 14 of the receiving end may be transmitted to the sender. The analyzed data of the mental state and/or the physiological condition are directly sent to the display 35 on the side of the sensor, and categorized into basically the four representative frequency bands, and displayed as shown in FIG. 10 and FIG. 12.

Next, for example, heartbeats are measured by the sensor 10 as the vital sign data as below. The heartbeats and the pulses tend to be slow when he/she is calm; on the other hand, when he/she is excited or nervous, the heartbeats and pulses tend to be fast. Thus, a change of the heartbeats and the pulses reflect a mental or physical activity.

Examples of methods for detecting heartbeats and pulses include a method by which a change in reflectance of a skin surface due to a change of a skin surface brought about by pressing pulse waves is detected by an LED and a light-intercepting element, and a method by which a change of pulse waves of a skin is detected directly by a pressure sensor. A communication apparatus such as a cellular phone in the form of a watch is suitable for this method.

When an operator of the communication apparatus wants to transmit his/her mental state and/or physiological condition to the receiving end, or when the operator communicates while checking his/her mental state and/or physiological condition, the sensor 10, which detects heartbeats by the foregoing method, is connected to an interface 16, and vital sign data are measured based on the heartbeats and inputted to the transmitter 11 and transmitted. Thereafter the vital sign are displayed on the display 25 of the receiving end, or displayed on the display 35 of the sending end.

For example, when the average pulse rate of an operator is P100 (about 60 to 80 times/minute), and when the measured pulse rate is in the vicinity of P100, the measured value is displayed as an origin or an average in the display of FIG. 10 or FIG. 12. For example, when the pulse rate becomes greater than P100 the calescence point moves towards the right in the parameter 1 in FIG. 10. When pulse rate is less than P100 the calescence point moves towards the left.

Since only one parameter is used, the displacement is one-dimensional either in the vertical or horizontal direction. However, when another parameter is used together to indicate data based on a multivariate analysis, the data are displayed two-dimensionally.

Alternatively, a method by which coordinates or quadrants are specified in advance as "relax", "usual", and "nervous" respectively can be used. For example, when P100 is a standard, the numeric value smaller than P100 by a predetermined amount, for example, not more than 90% is judged "relax". In the same manner, more than 90% and not more than 150% is judged "usual", and not less than 150% is judged "nervous".

The criteria for this judgement may be changed according to physical data such as individual differences, age, and temperature to be described later. For example, when judged "usual", a mark is flashed in the first quadrant. In the same manner, a mark is flashed in the second quadrant and the fourth quadrant when judged "relax" and "nervous", respectively.

Further, characters such as "RELAX", "USUAL", "NERVOUS" may be displayed, or, colors of characters and the background may be changed. For example, "RELAX" is blue, "USUAL" is green, and "NERVOUS" is yellow or red.

Alternatively, the background sound may be changed. Or the sound of transmitted voice and received voice outputted from a speaker may be strengthened or weakened according to results of emotion judgement to emphasize communication or hide his/her emotions.

Further, when displaying the parameter on the side of the sender, pulse rate data given by the data (physical data of surroundings) analyzer 44 of the sender are transmitted to the display 35 of the sending end and displayed therein. Alternatively, the pulse rate data given by the data (physical data of surroundings) analyzer 44 of the sending end are transmitted to the receiver 13 and displayed on the display 25 of the receiver 13.

In this case, the mental state and/or the physiological state of the sending end detected in accordance with the pulse rate can be displayed on both the sending and receiving ends. Even in this case, as in the case of the brain wave, the transmitter 11 of the sending end can be provided with a switch for permitting or not permitting the apparatus to transmit the data of the mental state and/or the physiological condition of the operator; or the receiver 13 of the receiving end can be provided with a switch for permitting or not permitting the apparatus to receive the data; or the display 35 of the receiving end can be provided with a switch for permitting or not permitting the apparatus to display the data of the mental state and/or the physiological condition; or the display 25 of the receiving end can be provided with a switch for permitting the apparatus to display the data of the mental state and/or the physiological condition of the operator. Thus, the operator can restrict display of the operator's mental state and physiological condition intentionally.

Alternatively, the vital sign data of the pulse rate measured by the sensor 10 are transmitted from the transmitter 11 without being analyzed and processed, and the vital sign are analyzed in the data (physical data of surroundings) analyzer 14 after being sent from the receiver 13, and categorized into basically the three representative mental states mentioned above, and as shown in FIG. 10 and FIG. 12, the data are displayed on the display 25 based on the three mental states.

Another modification example is as follows. When displaying the vital sign data on the side of the sender, the data measured at the sending end and analyzed by the data (physical data of surroundings) analyzer 14 of the receiving end are transmitted to the sending end. The analyzed data of the mental state and/or the physiological condition in accordance with the pulse rate, which are sent to the sender are directly sent to the display 35 of the sender, and the data are categorized into basically the three representative mental states mentioned above to be displayed as shown in FIG. 10 and FIG. 12.

Next, for example, body temperature is measured by the sensor 10 as vital sign data as below. The body temperature tends to be high when he/she is calm mentally because the peripheral blood vessels are expanded and artery blood flows into these blood vessels. On the other hand, the body temperature tends to be low when he/she is nervous because the peripheral blood vessels constrict and less artery blood flows into these blood vessels. The body temperature can be detected easily by using a temperature sensor such as a thermistor. A communication apparatus such as a cellular phone which is held by hands and is not an earphone type is suitable for this method. It is preferable that a temperature sensor such as a thermistor is provided on a part of the communication apparatus body 15 which is held by hands of the operator.

When an operator of the communication apparatus wants to transmit his/her mental state and/or physiological condition to the receiving end, and when the operator communicates while checking his/her mental state and/or physiological condition, the sensor 10, which detects the temperature of hands in the foregoing manner is turned on so as to measure vital sign data based on the detected temperature of the hands and input the data to the transmitter 11 via the interface 16. The data is then displayed on the display 25 of the receiving end and/or the display 35 of the sending end as described above.

For example, when the average temperature of the hands of an operator is S100 (about 31.1° C.), and the measured body temperature is in the vicinity of S100 the measured value is displayed as an origin or an average in display of FIG. 10 or FIG. 12, and, for example, when the temperature of the hands becomes more than S100 the calescence point moves towards the right in the parameter 1 in FIG. 10. When the temperature of hands is less than S100 the calescence point moves towards the left.

Alternatively, a method by which coordinates or quadrants are specified in advance as "relax", "usual", and "nervous" respectively. For example, when S100 is a standard, +0.2° C. to +0.4° C. is judged to be "relax". In the same manner, −0.1° C. to +0.1° C. is judged to be "usual", and −0.2° C. to −0.4° C. is judged to be "nervous". Alternatively, during a usual conversation over a phone, etc, a rise in temperature of the hands by 0.1° C. or more from a standard temperature which is detected in the beginning of transmission may be judged to be "relax", and in the same manner, a fall in temperature of the hands by 0.1° C. or more may be judged to be "nervous", and other temperatures are judged to be "usual". The criteria for this judgement may be changed according to such factors as individual differences or age.

Further, since the body temperature is influenced by surrounding temperature to some extent, the temperature of the hands may be corrected based on the surrounding temperature detected by another sensor 10 of a thermistor which is provided on a portion not in contact with the operator. When "usual" is judged, a mark blinks in the first quadrant. In the same manner, a mark is flashed in the second quadrant and in the fourth quadrant when "relax" and "nervous" are judged respectively.

Alternatively, characters such as "RELAX", "USUAL", "NERVOUS" may be displayed, or, colors of characters and the background may be changed. For example, "RELAX" is blue, "USUAL" is green, and "NERVOUS" is yellow or red. Further, the background sound may be changed.

Further, the sound of transmitted voice and received voice outputted from a speaker may be strengthened or weakened according to results of emotion judgement so as to emphasize connection or hide his/her emotions.

Further, another modification example is as follows. When displaying the vital sign data on the side of the sender, the body temperature data given by the data (physical data of surroundings) analyzer 44 of the sending end may be sent to the display 35 of the sending end. Alternatively, the body temperature data of the data (physical data of surroundings) analyzer 44 of the sending end may be sent to the receiver 13 and displayed on the display 25 of the receiving end. In this case, a mental state and/or physiological condition of the sending end analyzed according to the body temperature can be displayed on both the sending and receiving ends.

Even in this case, the transmitter 11 of the sending end can be provided with a switch for permitting or not permitting the apparatus to transmit the data of the mental state and/or the physiological condition of the operator; or the receiver 13 of the receiving end can be provided with a switch for permitting or not permitting the apparatus to receive the data; or the display 35 of the sending end can be provided with a switch for permitting or not permitting the apparatus to display the data of the mental state and/or the physiological condition; or the display 25 of the receiving end can be provided with a switch for permitting or not permitting the apparatus to display the data of the mental and/or the physiological condition of the operator. Thus, the operator can restrict display of the operator's mental state and/or physiological condition intentionally.

Alternatively, the vital sign data based on the measured body temperature are transmitted from the transmitter 11 without being analyzed and processed, and inputted via the receiver 13 to the data (physical data of surroundings) analyzer 14, and analyzed in the data (physical data of surroundings) analyzer 14. The data are then categorized into basically the three representative mental states mentioned above, and, as shown in FIG. 10 and FIG. 12, displayed on the display 25 based on the mental state thus categorized.

Another modification example is as follows. When displaying vital sign data on the side of the sender, the data of the body temperature detected in the sender and analyzed by the data (physical data of surroundings) analyzer 14 of the receiving end are transmitted to the sender. The analyzed data of the mental state and/or the physiological condition based on the body temperature, which were sent to the sender, are directly sent to the display 35 of the sender, and the data are categorized into basically the three representative mental states mentioned above, and displayed as shown in FIG. 10 and FIG. 12.

Next, for example, blinks of an eye measured by the sensor 10 are used as vital sign data as below. The blinks reflect mental (psychological) activities such as "nervousness" or "interest". When he/she pays attention to outside, frequency of blinks is low. When he/she pays attention to inside, frequency of blinks is high. That is, when things he/she is watching are interesting or attractive, blinks are usually restrained, but once free from the state, blinks tend to increase temporarily on the rebound.

In other words, when things he/she is observing are interesting or attractive, blinks are usually restrained. Released from the state, frequency of blinks tends to increase temporarily. Thus, frequency of blinks can also be used as a visible evaluation barometer (parameter).

Movement of blinks can be detected easily by detecting movement of edges of an image taken by a CCD or CMOS image sensor. Communication apparatuses such as a cellular phone with a CCD or CMOS image sensor, a TV telephone, and a PDA communication apparatus with a camera are suitable for this method.

It is preferable that a CCD or CMOS image sensor is provided on that part of the communication apparatus body 15 as the sensor 10 from which images of the entire face or at least the area around the eyes can be taken.

When an operator of the communication apparatus wants to communicate his/her mental state and/or physiological condition to the receiving end, or when the operator communicates while checking his/her mental state and/or physiological condition, the sensor 10 for detecting the blinks in the foregoing manner is turned on so as to measure vital sign data based on blinks and input the data to the transmitter 11 via the interface 16. The data is then displayed on the display 25 of the receiving end and the display 35 of the sending end.

For example, when the average frequency of blinks of an operator is M100 (about 45 times/minute), and when the measured frequency of blinks is in the vicinity of M100 the measured value is indicated as an origin or an average in display of FIG. 10 or FIG. 12, and, for example, when the frequency of blinks becomes more than M100 the calescence point moves towards the right in the parameter 1 in FIG. 10. When the frequency of blinks becomes less than M100 the calescence point moves towards the left. Since only one parameter is employed, the displacement is one-dimensional in the direction of ordinate or abscissa. However, when another parameter is added for a multivariate analysis, the parameters are displayed two-dimensionally.

Alternatively, a method by which coordinates or quadrants are specified in advance as "relax", "usual", and "nervous" respectively is available. For example, when M100 is a standard, about one-third of M100 (10 times/minute) is judged to be "nervous" or "excited". When the frequency is increased suddenly (by over 60, or 45 times/minute), it is judged to be "relax" or "free from tension". Other frequency is judged to be "usual". The criteria for this judgement may be changed according to such factors as individual differences or age.

When "usual" is judged, a mark blinks in the first quadrant. In the same manner, a mark blinks in the second quadrant and the fourth quadrant when "relax" and "nervous", "interested" or "concentrating" are judged respectively.

Further, characters such as "RELAX", "USUAL", "NERVOUS AND INTERESTED" may be displayed, or, colors of characters may be changed. For example, "RELAX" is blue, "USUAL" is green, and "NERVOUS-INTERESTED" is red. Further, the background sound may be changed, or the sound of transmitted voice and received voice outputted from a speaker may be strengthened or weakened according to the result of emotion judgement so as to emphasize communication or hide his/her emotions.

Further, another modification example is as follows. When displaying the frequency data of blinks on the side of the sender, the frequency data of blinks sent from the data (physical data of surroundings) analyzer 44 may be sent to the display 35 of the sending end. Alternatively, the frequency data of blinks given by the data (physical data of surroundings) analyzer 44 of the sender may be sent to the receiver 13 and displayed on the display 25 of the receiving end based on the frequency data of blinks received by the receiver 13. In this case, a mental state and/or a physiological condition of the operator detected in accordance with the frequency of blinks can be displayed on both the sending and receiving ends.

Even in this case, the transmitter 11 of the sending end can be provided with a switch for permitting or not permitting the apparatus to transmit the data of the mental state and/or the physiological condition of the operator; or the receiver 13 of the receiving end can be provided with a switch for permitting or not permitting the apparatus to receive the data and; or the display 35 of the receiving end can be provided with a switch for permitting or not permitting the apparatus to display the data of the mental state and/or the physiological condition; or the display 25 of the receiving end can be provided with a switch for permitting or not permitting the apparatus to display the data of the mental and/or the physiological condition of the operator. Thus, the operator can restrict display of the operator's mental and/or physiological condition intentionally.

Alternatively, the vital sign data of the frequency of blinks measured by the sensor 10 are transmitted from the transmitter 11 to the receiver 13 without being analyzed or processed, and the vital sign data are inputted and analyzed in the data (physical data of surroundings) analyzer 14 via the receiver 13, and categorized into basically the three representative mental states mentioned above, and as shown in FIG. 10 and FIG. 12, the data are displayed based on the three mental states thus categorized.

Another modification example is as follows. When displaying the frequency data of blinks on the side of the sender, the frequency data of blinks which are measured by the sending end and processed by the data (physical data of surroundings) analyzer 14 of the receiving end may be transmitted to the sender. The analyzed data of the mental state and/or the physiological condition based on the frequency of blinks, which were sent to the sender, are directly sent to the display 35 of the sender. Thereafter, the data are categorized into basically the three representative mental states mentioned above, and displayed as shown in FIG. 10 and FIG. 12.

Next, for example, pupil reaction is measured by the sensor 10 as vital sign data as below. Pupils give rise to light reflex and near-by reflex, and they further change according to mental (psychological) activities. The pupil reaction reflects mental (psychological) activities such as "interest". When he/she is interested or nervous, the relative rate of increase of the pupil area is high and it increases in size (mydriasis). When he/she is not interested or not nervous, pupil size is reduced (myosis).

A change in size of the pupil can be detected more easily by detecting movement of edges of an image taken by a CCD or CMOS image sensor. Communication apparatuses such as a cellular phone having a CCD or CMOS image sensor, a TV telephone, and a PDA communication apparatus with a camera are suitable for this method. Especially, a communication apparatus such as an earphone type cellular phone is suitable for this method.

It is preferable that a CCD or CMOS image sensor is provided on that part of the communication apparatus body 15 as the sensor 10 from which images of the whole eye or the pupil can be measured.

When an operator of the communication apparatus wants to communicate his/her mental state and physiological condition to the receiving end, and when the operator communicates while checking his/her mental state and/or physiological condition, the sensor 10 for detecting the pupil size in the foregoing manner is turned on so as to measure vital sign data based on the pupil size and input it to the communication apparatus via the interface 16.

For example, if the average pupil size of an operator is D100 (increasing rate of 0), and when the measured pupil size is in the vicinity of D100 the measured size is indicated as an origin or an average in display of FIG. 10 or FIG. 12. For example, when the pupil size is more than D100 the calescence point moves towards the right in the parameter 1 in FIG. 10. When the pupil size is less than D100 the calescence point moves towards the left. Since only one parameter is employed, the displacement is one-dimensional, either in the direction of ordinate or abscissa. However, when other parameters are added for a multivariate analysis, the parameters are displayed multi-dimensionally.

Alternatively, a method by which coordinates or quadrants are specified in advance as "interested", "usual", and "not interested", or "dislike" respectively is available. For example, when D100 (increasing rate of 0) is a standard, an increase in pupil size (mydriasis) within a range of not less than 10% and not more than 30% with respect to D100 is judged to be "interested". A decrease in pupil size (myosis) within a range of not less than 10% and not more than 20% with respect to D100 is judged to be "not interested" or "dislike". The other range is judged to be "usual".

The criteria for this judgement may be changed according to such factors as individual differences or age. When the vital sign data is judged to be "usual", a mark blinks in the first quadrant. In the same manner, a mark is flashed in the second quadrant and in the fourth quadrant when "interested" and "not interested" or "dislike" are judged respectively.

Further, characters such as "INTERESTED", "USUAL", "NOT INTERESTED OR DISLIKE" may be displayed, or, colors of characters may be changed, so that "INTERESTED" is blue, "USUAL" is green, and "INTERESTED-DISLIKE" is red. Further, the background sound may be changed, or the sound of transmitted voice and received voice outputted from a speaker may be strengthened or weakened according to the result of emotion judgement so as to emphasize communication or hide his/her emotions.

Another modification example of the present embodiment is as follows. When displaying on the side of the sender, the data of changing rate of pupil size given by the data (physical data of surroundings) analyzer 44 may be sent to the display 35 of the sending end and displayed therein. Alternatively, the data of changing rate of pupil size given by the data (physical data of surroundings) analyzer 44 may be sent to the receiver 13 and displayed on the display 25 of the receiving end based on the data of changing rate of pupil size received by the receiver 13. In this case, the mental state and/or the physiological condition of the operator detected in accordance with the changing rate of the pupil size can be displayed on both the sending and receiving ends.

Even in this case, the transmitter 11 of the sending end can be provided with a switch for permitting or not permitting the apparatus to transmit the data of the mental state and/or the physiological condition of the operator; or the receiver 13 of the receiving end can be provided with a switch for permitting or not permitting the apparatus to receive the data; or the display 35 of the receiving end can be provided with a switch for permitting or not permitting the apparatus to display the data of the mental state and/or the physiological condition; or the display 25 of the receiving end can be provided with a switch for permitting or not the apparatus to display the data of the mental state and/or the physiological condition of the operator. Thus, the operator can restrict display of the data of the operator's mental state and physiological condition intentionally.

Alternatively, the vital sign data of pupil size measured by the sensor 10 are transmitted from the transmitter 11 to the receiver 13 without being analyzed or processed, and the vital sign data inputted via the receiver 13 are analyzed in the data (physical data of surroundings) analyzer 14, and categorized into basically the three representative mental states mentioned above, and displayed as shown in FIG. 10 and FIG. 12 based on the three mental states thus categorized.

Another modification example is as follows. When displaying on the side of the sender, the data of changing rate of pupil size measured by the sender and analyzed by the data (physical data of surroundings) analyzer 14 of the receiving end may be transmitted to the sender. The analyzed data of the mental state and/or the physiological condition in accordance with the changing rate of pupil size, which were sent to the sender, are directly sent to the display 35 of the of the sender. Thereafter, the data are categorized into basically the three representative mental states mentioned above, and displayed as shown in FIG. 10 and FIG. 12.

Next, skin resistance is measured by the sensor 10 as vital sign data as below. The skin resistance is increased when he/she is mentally calm, and the skin resistance is reduced when he/she is under stress by feeling mentally (psychologically) nervous or excited.

Methods for directly detecting skin resistance include (1) an electric potential method, (2) a conduction method by direct current (a simple circuit, a wheastone bridge circuit, a compensation circuit, a capacitor circuit), (3) a conduction method by alternating current (a wheastone bridge circuit) and the like.

A communication apparatus such as a telephone which is held by hands and not an earphone type is suitable for these methods. It is preferable that the sensor 10 for detecting skin resistance is provided on that part of the communication apparatus body 15 held or grabbed by the operator.

When an operator of the communication apparatus wants to communicate his/her mental state and/or physiological condition to the receiving end, and when the operator communicates while checking his/her mental state and/or physiological condition, the sensor 10 for detecting skin resistance in the foregoing manner is turned on so as to measure vital sign data based on the skin resistance of the hand and input it to the transmitter 11 via the interface 16, and the data is displayed as described above.

For example, if the average skin resistance of the hand of an operator is R100 (about 15,000Ω/cm$^2$), and when the measured skin resistance is in the vicinity of R100 the measured resistance is indicated as an origin or an average in the display of FIG. 10 or FIG. 12. When the skin resistance is more than R100 the calescence point moves towards the right in the parameter 1 in FIG. 10. When the skin resistance is less than R100 the calescence point moves towards the left. Since only one parameter is employed, the displacement is one-dimensional, either in the direction of ordinate or abscissa. However, when other parameters are added for a multivariate analysis, the parameters are displayed multi-dimensionally.

Alternatively, a method by which coordinates or quadrants are specified in advance as "relax", "usual", and "excited", or "nervous" respectively is available. For example, when S100 is a standard, about 5 times to 20 times S100 is judged to be "relax", and one-fifth to one-twentieth of S100 is judged to be "excited" or "nervous". The other range is judged to be "usual".

Further, during a conversation over a phone, etc., a transient change in skin resistance, reducing abruptly in a few seconds with respect to the standard the skin resistance of the hand at the beginning of conversation, may be judged to be "excited". This probably results from perspiration due to excitement or nervousness. The criteria for this judgement may be changed according to individual differences or age. Since the body temperature of hands is influenced by surrounding temperature to some extent, the temperature of hands may be corrected based on the surrounding temperature detected by another sensor 10 of a thermistor which is provided on a portion not in contact with the operator.

When "usual" is judged, a mark may be flashed in the first quadrant. In the same manner, a mark may be flashed in the second quadrant, in the fourth quadrant when "relax" and "nervous" or "excited" are judged, respectively.

Further, characters such as "RELAX", "USUAL", "NERVOUS AND EXCITED" may be displayed, or, colors of characters may be changed. For example, "RELAX" is blue, "USUAL" is green, and "NERVOUS" is yellow or red. Further, the background sound may be changed, or the sound of transmitted voice and received voice outputted from a speaker may be strengthened or weakened according to the result of emotion judgement so as to emphasize communication or hide his/her emotions.

A modification example is as follows. When displaying on the side of the sender, the skin resistance data from the data (physical data of surroundings) analyzer 44 may be sent to the display 35 of the sending end and displayed therein. Alternatively, the skin resistance data given by the data (physical data of surroundings) analyzer 44 may be sent to the receiver 13 and displayed on the display 25 of the receiving end based on the skin resistance data received by the receiver 13.

In this case, the mental state and/or the physiological condition of the operator detected in accordance with the skin resistance data can be displayed on both the sending and receiving ends. Even in this case, the transmitter 11 of the sender can be provided with a switch for permitting or not permitting the apparatus to transmit the mental state and/or the physiological condition of the operator; or the receiver 13 of the receiving end can be provided with a switch for permitting or not permitting the apparatus to receive the data; or the display 35 of the receiving end can be provided with a switch for permitting or not permitting the apparatus to display the data of the mental state and/or the physiological condition; or the display 25 of the receiving end can be provided with a switch for permitting or not permitting the apparatus to display the data of the mental state and/or the physiological condition of the operator. Thus, the operator can restrict display of the operator's mental state and physiological condition intentionally.

Alternatively, the vital sign data of skin resistance measured by the sensor 10 are transmitted from the transmitter 11 without being analyzed or processed, and vital sign data are analyzed in the data (physical data of surroundings) analyzer 14 after being sent from the receiver 13, and categorized into basically the three representative mental states mentioned above, and displayed on the display 25 as shown in FIG. 10 and FIG. 12.

Another modification example is as follows. When displaying on the side of the sender, the data of the analyzed brain wave frequency measured by the sender and analyzed by the data (physical data of surroundings) analyzer 14 of the receiving end may be transmitted to the sender. The analyzed data of the mental state and/or the physiological condition are directly sent to the display 35 on the side of the sensor, and categorized into basically the four representative frequency bands, and displayed as shown in FIG. 10 and FIG. 12.

Next, for example, sound is measured as the vital sign data as below. An example of a method for displaying emotions of the sending end analyzed in accordance with sound frequency and sound power of the sending end is described concretely with reference to FIG. 16.

Figure 17:
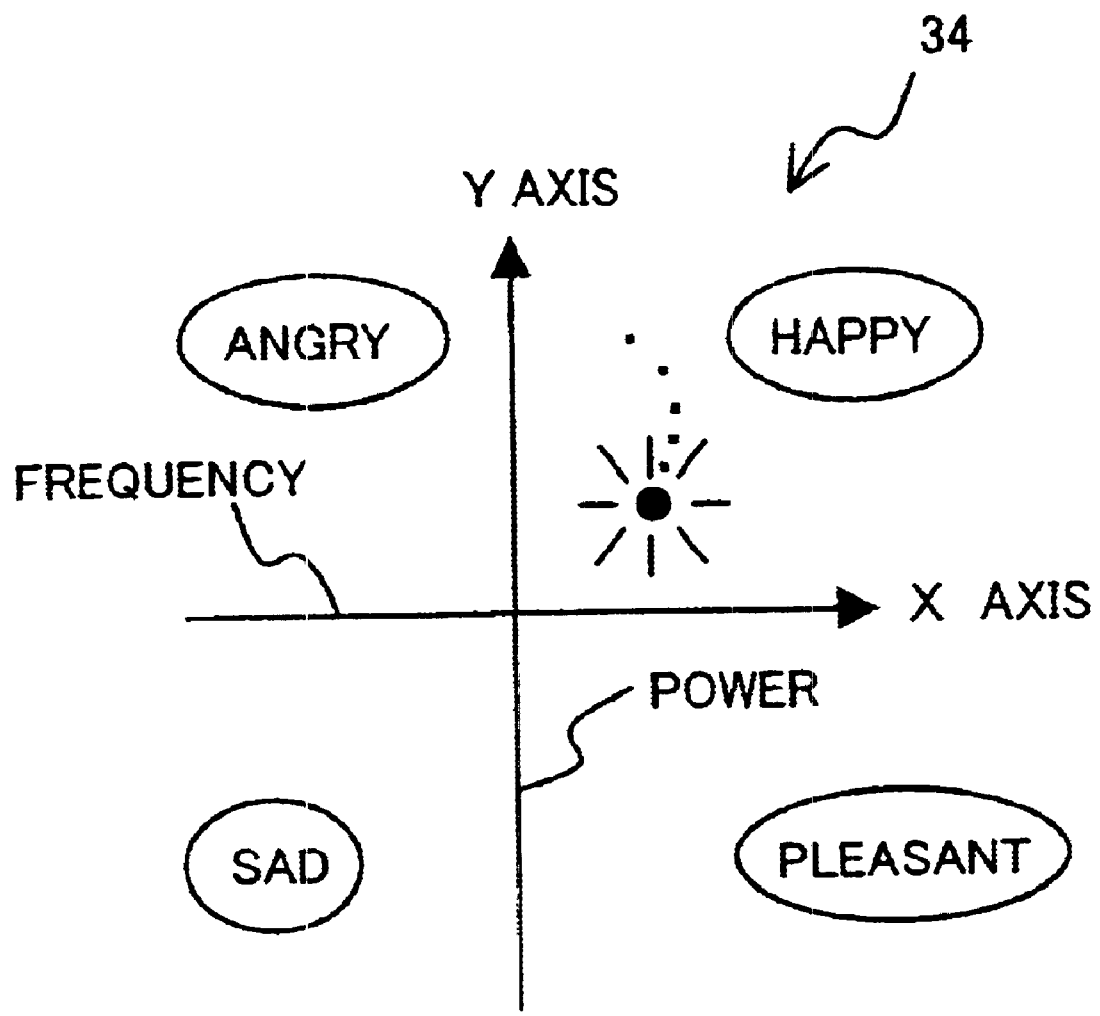
FIG. 17 is an explanatory drawing showing still another display example of the display in the communication apparatus.

First, frequency of sound data is sampled and averaged by a frequency analyze module 33 in real time based on sound data of the sender. Here, "real time" with the intervals of around 0.1 to 1 second is sufficient as will be clear from display method described later. At the same time, power of the sound data is also sampled and arranged by a power analyze module 32. In the display 25, deviation from the frequency mean value is the X axis, and deviation from the power mean value is the Y axis (FIG. 17).

X can be expressed by equations as following. Y is also expressed in the same manner. Note that, n is a natural number.

| sampling value | mean value | value of X |
| --- | --- | --- |
| fs (1) | fm (1) = fs (1) | fs (1) − fm (1) |
| fs (2) | fm (2) = (fs (1) + fs (2))/2 | fs (2) − fm (2) |
| fs (3) | fm (3) = (fs (1) + ... + fs (3))/3 | fs (3) − fm (3) |
| . | . | . |
| . | . | . |
| . | . | . |
| fs (n) | fm (n) = (fs (1) + ... + fs (n))/n | fs (n) − fm (n) |

Since a high frequency voice is high key and low frequency voice is low key, these frequency data can be used as a parameter for indicating emotions such as easy and uneasy.

Also, since a high power voice is considered to reflect strong emotions and low power voice is considered to reflect weak emotions, these voice power data can be used as a parameter for indicating strength and weakness of emotions. According to the X axis which indicates deviation from the mean frequency, and the Y axis which indicates deviation from the mean power, "happy" is indicated in the first quadrant, "angry" in the second quadrant, "sad" in the third quadrant, "pleasant" in the fourth quadrant. In this way, the four emotions can be indicated. These emotions are outputted realtime to the display 25 and displayed, for example, as a mark 34.

By displaying real time data of the sender as the mark 34 with the coordinate axis while he/she is talking on the phone, the receiving end can judge emotions of the sending end more objectively and more appropriately based on the displayed data. When the receiving end talks with the same sender, the mean value used in the past communication also can be used. Since this method can be processed only by the terminal of the receiving end, coordination between the receiving end and the sending end is not needed. Thus, this method also can be applied to current cellular phones easily.

Alternatively, intonation or stress on speech may be used to judge emotions of an operator as "joy", "anger", or "fright". For example, when a sentence ends on the rise, it is judged to be "joy". On the other hand, when a sentence ends on the fall, or the voice is low and strong, it is judged to be "anger". When the sound is weak and its frequency is high, it is judged to be "fright". According to the sound pressure, sound frequency, and their change over time, the data (physical data of surroundings) analyzer 14 gives judgement in this way using a microphone of a telephone as the input section.

Though three types of emotions are judged in the example, more types of emotions such as "surprised", "vulnerable", and "dislike" can be judged approximately by calculating a minimum value of inner product values based on a database by a VQ technique (vector quantization) in which emotions reflected by the sound are quantized. Communication apparatuses including all kinds of the telephones are suitable for this method.

When an operator of the communication apparatus wants to communicate his/her mental state and/or physiological condition to the receiving end, and when the operator communicates while checking his/her mental state and/or physiological condition, the sensor 10 for judging emotions based on sound is turned on so as to measure the vital sign data based on the judgement in accordance with sound and input it to the transmitter 11 via the interface 16, and the data is displayed as described above.

Alternatively, a method by which coordinates or quadrants are specified in advance as "joy", "anger", and "fright", "surprised", "vulnerable", and "dislike" respectively can be used. When a sentence ends on the rise, it is judged to be "joy". On the other hand, when a sentence ends on the fall, or the voice is low and strong, it is judged to be "anger". When the voice is weak and its frequency is high, it is judged to be "fright". The emotions of "surprised", "vulnerable", and "dislike" are judged, for example, by using the VQ technique based on sound reflecting emotions.

That is, a compressed database concerning voice sound which typically reflects emotions such as "surprised", "vulnerable", "dislike" is created by VQ. The inner products of the measured sound and the compressed database of the respective emotions by VQ are calculated, and the emotion of the database which gave the minimum value is judged to be an emotion of the measured sound. This criteria for this judgement may be changed according to individual differences or age.

Figure 11:
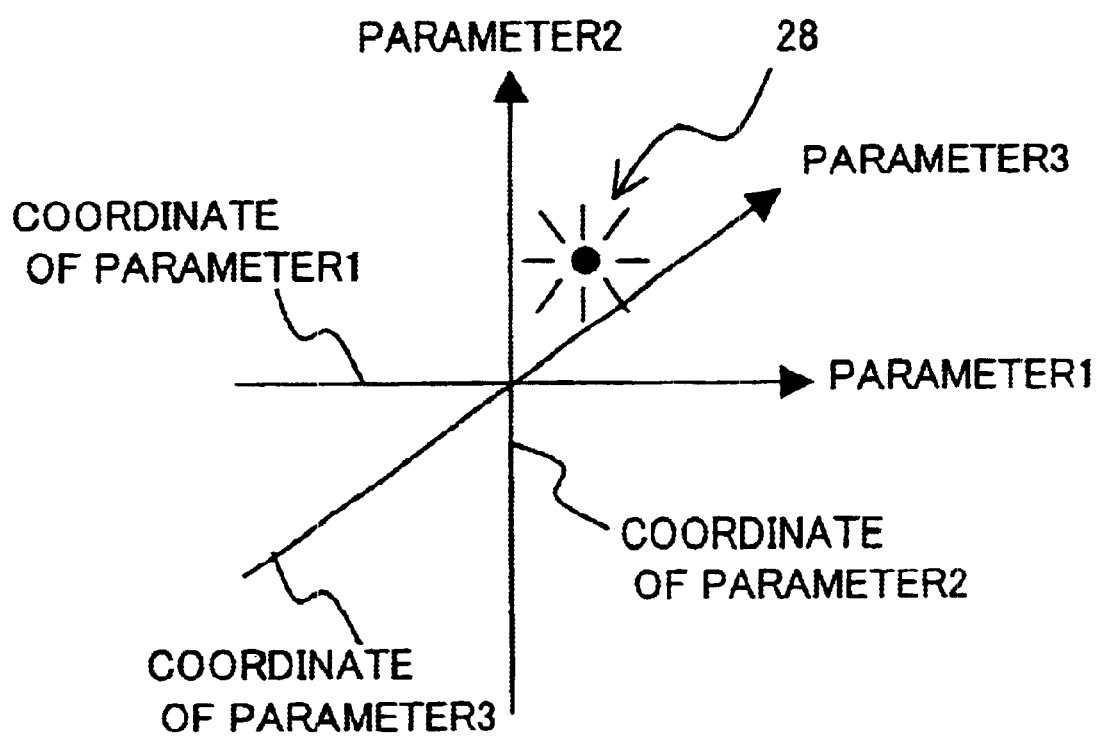
FIG. 11 is an explanatory drawing showing still another display example of the display in the communication apparatus.
Figure 12:
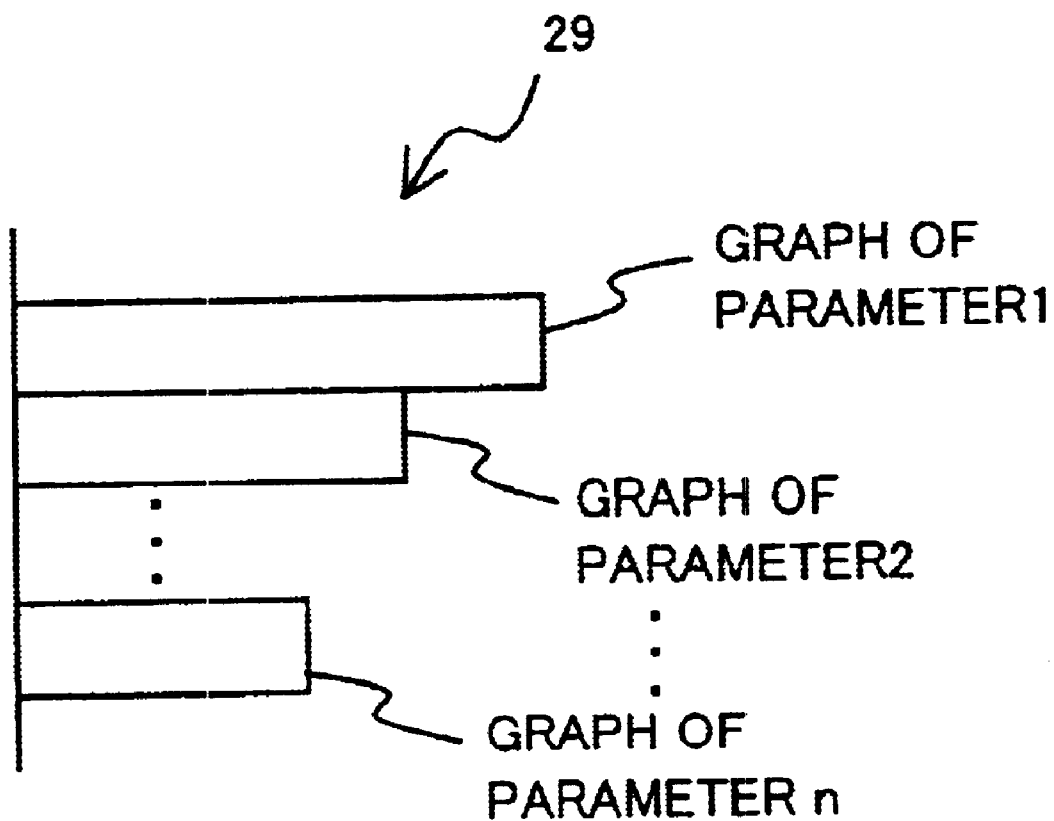
FIG. 12 is a graph showing still another display example of the display in the communication apparatus.

For example, when "joy", "anger", "fright", "surprised", "vulnerable", and "dislike" are indicated in parameters of FIG. 11 or FIG. 13, emotions can be displayed multi-dimensionally. Further, a mark may be flashed in quadrants of the parameters respectively judged, or characters such as "JOY", "ANGER", "FRIGHT", "SURPRISED", "VULNERABLE", and "DISLIKE" may be displayed.

Alternatively, colors of characters may be changed. For example, "RELAX" is blue, "USUAL" is green, and "NERVOUS" is yellow or red, or the background sound may be changed. Further, the sound of transmitted voice and received voice outputted from a speaker may be strengthened or weakened according to the result of emotion judgement so as to emphasize communication or hide his/her emotions.

Another example of judging method based on sound is as follows. The emotions "joy", "anger", "sorrow", and "usual", etc., are judged based on sound data including the highest frequency, the lowest frequency, a difference between the highest frequency and the lowest frequency, the maximum amplitude, the average amplitude, the longest duration of speech, and distribution of duration within a predetermined sampling time for judgement. The data concerning the emotions are sampled in advance. The "usual" is set to be standard, and deviation from the standard is quantized as a feature parameter and stored in a database for each emotion.

The quantized data may be quantized, and as in the foregoing example, for example, the emotion which gives the minimum inner product value of the data compressed by VQ or sample sound and the database may be regarded as the emotion of the sample sound.

As a modification example, when displaying on the side of the sender, the data of judged emotion of sound given by the data (physical data of surroundings) analyzer 44 of the sender may be sent to the display 35 of the sending end.

Alternatively, the data of the judged emotion of sound of the data (physical data of surroundings) analyzer 44 of the sending end may be sent to the receiver 13 and may be displayed on the display 25 of the receiving end.

In this case, the mental state and/or the physiological condition of the sending end analyzed according to the judged emotion of sound of the operator can be displayed on both the sending and receiving ends. Even in this case, the transmitter 11 of the sending end can be provided with a switch for permitting or not permitting the apparatus to transmit the data of the mental state and/or the physiological condition of the operator; or the receiver 13 of the receiving end can be provided with a switch for permitting or not permitting the apparatus to receive the data; or the display 35 of the sending end can be provided with a switch for permitting or not permitting the apparatus to display the data of the mental state and/or the physiological condition; or the display 25 of the receiving end can be provided with a switch for permitting or not permitting the apparatus to display the data of the mental state and/or the physiological condition of the operator. Thus, the operator can restrict display of the operator's mental state and physiological condition intentionally.

Alternatively, the vital sign data based on the sound measured by the sensor 10 are transmitted from the transmitter 11 without being analyzed or processed, and inputted via the receiver 13 to the data (physical data of surroundings)) analyzer 14, and analyzed in the data (physical data of surroundings)) analyzer 14. The data are then categorized into basically the three to six representative mental states mentioned above, and as shown in FIG. 11 and FIG. 13, displayed based on the mental states thus categorized. However, when other parameters are added for a multivariate analysis, the parameters are displayed multi-dimensionally.

Another modification example is as follows. When displaying on the side of the sender, the data of judged emotion of sound which were measured in the sending end and analyzed by the data (physical data of surroundings)) analyzer 14 of the receiving end are transmitted to the sending end. The analyzed data of the mental state and/or the physiological condition in accordance with the judged emotion of sound at the sending end are sent to the display 35 of the sending end, and the data are categorized into basically the three to six representative mental states mentioned above, and displayed as shown in FIG. 11 and FIG. 13.

Even in this case, as described above, by providing a switch for permitting or not permitting transmission or reception of the data of the mental state and/or the physiological condition of the operator; or by providing the display 25 or 35 with a switch for permitting or not permitting display of the mental and/or the physiological condition of the operator, the operator can restrict display of the operator's mental state and/or physiological condition intentionally.

Next, for example, strength of grip in holding the communication apparatus body 15 is measured as the vital sign data by the sensor 10 as below. When he/she is mentally and psychologically calm, the strength of grip tends to be weak. When he/she is excited, the grip tends to be strong. It is possible to detect the strength of grip easily by a pressure sensor. A communication apparatus such as a telephone which is held by hands and not an earphone type is suitable for this method. It is preferable that the pressure sensor is provided as the sensor 10 on that part of the communication apparatus body 15 held by the operator's hand.

When an operator of the communication apparatus wants to communicate his/her mental state and/or physiological condition to the receiving end, and when the operator communicates while checking his/her mental state and/or physiological condition, the sensor 10 for detecting the strength of grip in the foregoing manner is turned on so as to measure the vital sign data based on the strength of grip and input it to the transmitter 11 via the interface 16, and the data is displayed as described above.

For example, if the average strength of grip of an operator is H100 and when the measured strength of grip is in the vicinity of H100 the measured strength is indicated as an origin or an average in the display of FIG. 10 and FIG. 12, and, for example, when the strength of grip is more than H100 the calescence point moves towards the right in the parameter 1 in FIG. 10. When the strength of grip is less than H100 the calescence point moves towards the left.

Since only one parameter is employed, the displacement is one-dimensional either in the direction of ordinate or abscissa. However, when other parameters are added for a multivariate analysis, the parameters are displayed multi-dimensionally.

Alternatively, a method by which coordinates or quadrants are specified in advance as "relax", "usual", and "nervous" respectively is available. For example, when H100 is a standard, a 10% reduction of the strength of grip is judged to be "relax", and a 10% of more increase of the strength of grip is judged to be "nervous". The other range is judged to be "usual". The criteria for this judgement may be corrected according to individual differences or age etc.

When "usual" is judged, a mark blinks in the first quadrant. In the same manner, a mark is flashed in the second quadrant and in the fourth quadrant when "relax" and "nervous" are judged, respectively.

Alternatively, characters such as "RELAX", "USUAL", "NERVOUS" may be displayed, or, colors of characters may be changed. For example, "RELAX" is blue, "USUAL" is green, and "NERVOUS" is yellow or red. Further, the background sound may be changed, or the sound of transmitted voice and received voice outputted from a speaker may be strengthened or weakened according to the result of emotion judgement so as to emphasize communication or hide his/her emotions.

Another modification example is as follows. When displaying on the side of the sender, the data of grip strength outputted from the data (physical data of surroundings) analyzer 44 may be sent to or displayed on the display 35 of the sending end. Alternatively, the data of the strength of grip given by the data (physical data of surroundings) analyzer 44 of the sender may be sent to the receiver 13 and displayed on the display 25 of the receiving end based on the data of grip strength received by the receiver 13.

In this case, the mental state and/or the physiological condition of the operator in accordance with the strength of grip can be displayed on both the sending and receiving ends. Even in this case, by providing the transmitter 11 of the sender with a switch for permitting or not permitting the apparatus to transmit the data of the mental state and/or the physiological condition of the operator; or the receiver 13 of the receiving end with a switch for permitting or not permitting the apparatus to receive the data; or the display 35 of the receiving end with a switch for permitting or not permitting the apparatus to display the data of the mental state and/or the physiological condition; or the display 25 of the receiving with a switch for permitting or not permitting the apparatus to display the mental state and/or the physiological condition of the operator, the operator can restrict display of the operator's mental state and/or physiological condition intentionally.

Alternatively, the vital sign data of the strength of grip are transmitted from the transmitter 11 to the receiver 13 without being analyzed or processed, and inputted to and analyzed in the data (physical data of surroundings) analyzer 14, and categorized into basically the three representative mental states mentioned above, and displayed in the display 25 as shown in FIG. 10 and FIG. 12. As with the foregoing case, when only the parameter of the strength of grip is displayed, there exists only one parameter. Thus, the displacement is one-dimensional either in the direction of ordinate or abscissa.

Another modification example is as follows. When displaying on the side of the sender, the data of the strength of grip measured by the sender and analyzed by the data (physical data of surroundings) analyzer 14 of the receiving end may be transmitted to the sending end. The analyzed data of the mental state and/or the physiological condition sent to the sender are directly sent to the display 35 of the sender. Thereafter, the data are categorized into basically the three representative mental states mentioned above, and displayed as shown in FIG. 10 and FIG. 12.

A communication apparatus of the present invention, as described above, includes a transmitter and a receiver for communicating communication data having transmission data transmitted from an operator; and an estimating section for estimating a mental state and/or a physiological condition of the operator based on the communication data and for outputting an estimated quantity.

Therefore, since this arrangement makes it easier to grasp feelings or emotions, a physical condition, or surrounding environment of the sending end, communication between the sending end and the receiver can be made smooth.

The transmission data may include sound data. According to the arrangement, data which were transmitted unintentionally (strength or weakness of voice, a change of accent position, surrounding noise) are extracted from the sound data. Based on the extracted data, for example, feelings or emotions, a physical condition, or surrounding environment of the operator are estimated. Thus, the receiving end not only receives words of the sending end literally based on the sound data, but can grasp deeper meaning of the words.

The transmission data may include image data. According to the arrangement, data which were transmitted unintentionally (direction of view, blinks, pupil size, movement of lips, moisture of a mouth, facial expressions and facial colors, movement of a body, a posture, the number of people around the apparatus, brightness, and weather) are extracted from the image data. Based on the extracted data, for example, feelings or emotions, a physical condition, or surrounding environment of the sending end are estimated. Thus, the receiving end not only receives words of the sending end based on the image data literally, but can grasp deeper meaning of the words.

The communication apparatus may further include a vital sign sensor for measuring an operator's vital sign such as heartbeats, and the communication data may include the vital sign data. The communication apparatus may further include an environment sensor for measuring physical data such as temperature in the surrounding environment of the apparatus, and the communication data may include the physical data.

According to the arrangement, not only conventional transmission data such as sound data, character data, image data, and software data, but also vital sign data and physical data (electric potential of hand muscle, heartbeats, skin resistance, body temperature, and temperature on the side of an operator holding the communication apparatus body provided with a transmitter or a receiver therein) can be obtained as various data of a sending end or a receiver. Thus, it is possible to estimate the sending end's feelings and emotions, physical condition, and surrounding environment more easily.

It is preferable that the communication apparatus is provided a the communication apparatus body for storing at least one of the transmitter and the receiver, wherein said vital sign sensor is provided on a portion of the communication apparatus body which can be brought into contact with the operator.

According to the arrangement, since the vital sign sensor can be operated in direct or close contact with the operator of the sending or receiving end, the vital sign data of the sending end and the receiving end can be measured more exactly and more naturally.

The communication apparatus further includes a data memory for storing personal and social data of the operator, wherein said estimating section utilizes the personal and social data of the operator to obtain the estimated quantity based on the communication data.

According to the arrangement, since known personal and social data of the sender or the receiver can be refereed to, it is possible to calculate or estimate the sending end's feelings and emotions, physical condition, and surrounding environment more exactly.

In the communication apparatus, the estimating section includes a function of outputting the estimated quantity to receiving end either directly or after processing it. According to the arrangement, since the receiving end and the sending end can share the estimated quantity, content of the communication data can be checked to get feedback to the sender. Thus, the communication can be made even more smooth.

In the communication apparatus, the estimating section includes a function of outputting the estimated quantity to a sending end either directly or after processing it. According to the arrangement, since the receiving end and the sending end can share the estimated quantity, content of the communication data can be checked to get feedback to the sender. Thus, the communication can be made even more smooth.

In the communication apparatus, the estimating section expresses and outputs emotions "happy", "angry", "sad", "pleasant" of the operator based on the mental state and/or the physiological condition of the operator. According to the arrangement, by taking some aspects of human emotions, the receiving end can judge the mental state of the sending end more quickly and more appropriately.

In the communication apparatus, the estimating section outputs the estimated quantity in the form of processed data such as tables, graphs, or figures, facial expressions, and colors. According to the arrangement, feelings and emotions, physical condition, surroundings of the sender can be indicated more easily and more concretely.

The communication apparatus has a display for displaying image data included in the communication data, wherein said estimating section displays the estimated quantity on the display side by side with or over the image data. According to the arrangement, by comparing actual images of the sender with the estimated feelings and emotions, physical condition, surrounding environment of the sender, the receiver can make judgement more exactly.

The communication apparatus includes a selection section, provided on at least one of the transmitter and the receiver, for permitting or not permitting transmission or reception of the communication data, or permitting or not permitting output of the communication data.

According to the arrangement, permission to transmit or receive data which the sending end sends unintentionally can be left to a judgement of both the sender and the receiver. Thus, when the estimated quantity is not needed, trouble in communication can be avoided.

The communication apparatus includes a changing output section for changing the transmission data based on the estimated quantity. According to the arrangement, communication can be made more smooth by changing transmission data, for example, by changing transmitted or received sound outputted from a speaker to emphasize or hide emotions by the changing output section.

As described, according to a communication method of the present invention, when an operator communicates using communication data including transmission data transmitted from the operator, a mental state and/or a physiological condition of the operator is estimated based on the communication data and outputted.

In the communication method, personal and social data of the operator are stored, and the mental state and/or the physiological condition of the operator are estimated and outputted, taking into consideration the personal and social data of the operator.

In the communication method, an operator's vital sign data such as heartbeats are measured, and said vital sign data are communicated with the communication data.

According to the foregoing methods, a receiving end (or a sending end) can grasp feelings and emotions, physical condition, and surroundings of the sender more easily. Thus, communication between the sending end and the receiver can be made even more smooth.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A communication apparatus comprising:
    a transmitter and a receiver for communicating communication data including transmission data concerning an operator; and
    an estimating section for estimating a mental state and/or a physiological condition of the operator based on the communication data, and for outputting the mental state as an estimated quantity.

2. The communication apparatus set forth in claim 1, wherein the transmission data include voice data.

3. The communication apparatus set forth in claim 1, wherein the transmission data include image data.

4. The communication apparatus set forth in claim 1, further comprising an environment sensor for measuring physical data of surrounding environment,
    wherein said communication data include the physical data.

5. The communication apparatus set forth in claim 1, further comprising a data memory for storing personal and social data of the operator,
    wherein said estimating section utilizes the personal and social data of the operator to obtain the estimated quantity based on the communication data.

6. The communication apparatus set forth in claim 1, comprising a selection section, provided on at least one of the transmitter and the receiver, for permitting or not permitting transmission or reception of the communication data, or permitting or not permitting output of the communication data.

7. The communication apparatus set forth in claim 1 comprising a changing output section for changing the transmission data based on the estimated quantity.

8. The communication apparatus set forth in claim 1, wherein said estimating section includes a function of outputting the estimated quantity at a sending end either directly or after processing it.

9. The communication apparatus set forth in claim 1 further comprising a vital sign sensor for measuring an operator's vital sign as vital sign data,
    wherein said communication data include the vital sign data.

10. The communication apparatus set forth in claim 4, comprising a communication apparatus body for storing at least one of the transmitter and the receiver,
    wherein said vital sign sensor is provided on a portion of the communication apparatus body which can be brought into contact with the operator.

11. The communication apparatus set forth in claim 9, wherein the vital sign data are heartbeats.

12. The communication apparatus set forth in claim 1,
    wherein said estimating section is provided on a receiving end, and includes a function of outputting the estimated quantity either directly or after processing it.

13. The communication apparatus set forth in claim 12,
    wherein said estimating section expresses and outputs emotions "happy", "angry", "sad", "pleasant" of the operator based on the mental state and/or the physiological condition of the operator.

14. The communication apparatus set forth in claim 12, comprising a display for displaying an image data included in the communication data,
    wherein said estimating section displays the estimated quantity on the display side by side with or over the image data.

15. The communication apparatus set forth in claim 12,
    wherein said estimating section outputs the estimated quantity in the form of processed data.

16. The communication apparatus set forth in claim 15, wherein said form of processed data is tables, graphs, figures, facial expressions, or colors.

17. The communication apparatus set forth in claim 1,
    wherein said estimating section includes a function of outputting the estimated quantity to a sending end either directly or after processing it.

18. The communication apparatus set forth in claim 17,
    wherein said estimating section expresses and outputs emotions "happy", "angry", "sad", "pleasant" of the operator based on the mental state and/or the physiological condition of the operator.

19. The communication apparatus set forth in claim 17, comprising a display for displaying an image data included in the communication data,
    wherein said estimating section displays the estimated quantity on the display side by side with or over the image data.

20. The communication apparatus set forth in claim 17,
    wherein said estimating section outputs the estimated quantity in the form of processed data.

21. The communication apparatus set forth in claim 20, wherein said form of processed data is tables, graphs, figures, facial expressions, or colors.

22. A communication method in which, when an operator communicates using communication data including transmission data concerning the operator, a mental state of the operator is estimated based on the communication data and outputted.

23. The communication method set forth in claim 22,
wherein personal and social data of the operator are stored, and
the mental state and/or the physiological condition of the operator are estimated and outputted, taking into consideration the personal and social data of the operator.

24. The communication method set forth in claim 22, wherein an operator's vital sign data are measured, and said vital sign data are communicated with the communication data.

25. The communication method set forth in claim 24, wherein said vital sign data are heartbeats.

* * * * *